US007338769B2

(12) United States Patent
Firestein-Miller

(10) Patent No.: US 7,338,769 B2
(45) Date of Patent: Mar. 4, 2008

(54) METHODS FOR IDENTIFYING AGONISTS OF CYPIN

(75) Inventor: Bonnie Firestein-Miller, Hillsborough, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 11 days.

(21) Appl. No.: 11/033,909

(22) Filed: Jan. 12, 2005

(65) Prior Publication Data

US 2005/0214822 A1    Sep. 29, 2005

Related U.S. Application Data

(60) Provisional application No. 60/577,922, filed on Jun. 9, 2004, provisional application No. 60/535,512, filed on Jan. 12, 2004, provisional application No. 60/535,533, filed on Jan. 12, 2004, provisional application No. 60/535,534, filed on Jan. 12, 2004.

(51) Int. Cl.
| | |
|---|---|
| *G01N 33/53* | (2006.01) |
| *G01N 33/567* | (2006.01) |
| *G01N 33/542* | (2006.01) |
| *G01N 33/48* | (2006.01) |
| *G01N 33/00* | (2006.01) |
| *G01N 33/566* | (2006.01) |

(52) U.S. Cl. ........................ 435/7.1; 435/7.2; 435/7.21; 435/7.6; 435/7.8; 435/7.9; 436/501; 436/63; 436/86

(58) Field of Classification Search ...................... None
See application file for complete search history.

(56) References Cited

OTHER PUBLICATIONS

Akum, B F., et al., "Cypin regulates dendrite patterning in hippocampal neurons by promoting microtubule assembly", *Nature Neurosci. 7*:145, (2004), 145-152.
Arendt, Thomas , et al., "Plastic Neuronal Remodeling Is Impaired in Patients with Alzheimer's Disease Carrying Apolipoprotein 4 Allele", *J. Neurosci. 17*: 516, (1997),516-529.
Armstrong, D. D., "Rett syndrome neuropathology review 2000", *Brain Dev. 23 Suppl. 1*: S72, (Dec. 2001),S72-76.
Baker, R E., et al., "Growth of pyramidal, but not nonpyramidal, dendrites in long-term organotypic explants of neonatal rat neocortex chronically exposed to neurotrophin-3", *Eur. J. Neurosci. 10*: 1037, (1998), 1037-1044.
Becker, L. E., et al., "Dendritic atrophy in children with Down's syndrome", *Ann Neurol 20*: 520, (1986),520-526.
Belichenko, P. V., et al., "Rett syndrome: 3-D confocal microscopy of cortical pryamidal dendrites and afferents", *Neuroreport 5*:1509, (1994), 1509-1513.
Belichenko, P.V., et al., "Studies on the 3-dimensional architecture of dendritic spines and varicosities in human cortex by confocal laser scanning microscopy and Lucifer Yellow microinjections", *J.Neurosci.Methods 57*: 55, (1995),55-61.

Berry-Kravis, E. , et al., "Cyclic AMP metabolism in fragile X syndrome", *Ann. Neurol. 31*:22, (1992),22-26.
Bito, H , et al., "A critical role for a Rho-associated kinase in determining axon outgrowth in mammalian CNS neurons.", *Neuron 26*:431, (2000),431-441.
Boltshauser, E , et al., "Pterins in patients with Rett syndrome", *Am J Med Genet Suppl. 1*:317, (1986),317-321.
Ellezam, B , et al., "Inactivation of intracellular Rho to stimulate axon growth and regeneration", *Prog Brain Res 137*:371, (2002),371-380.
Firestein, B L., et al., "Cypin: a cytosolic regulator of PSD-95 postsynaptic targeting", *Neuron 24*: 659, (1999),659-672.
Fortes, P , et al., "Inhibiting expression of specific genes in mammalian cells with 5' end-mutated U1 small nuclear RNAs targeted to terminal exons of pre-mRNA.", *Proc. Natl. Acad. Sci. U. S. A. 100*: 8264, (2003),8264-8269.
Fukata, Y , et al., "CRMP-2 binds to tubulin heterodimers to promote microtubule assembly", *Nat. Cell Biol. 4*: 583, (2002),583-591.
Fuller, R. W., et al., "Serum uric acid in mongolism", *Science 137*:868, (1962),868-869.
Galvez, R , et al., "Somatosensory cortical barrel dendritic abnormalities in a mouse model of the fragile X mental retardation syndrome", *Brain Res 971*:83, (2003),83-89.
Gu Yongjun , et al., "Evidence That Collapsin Response Mediator Protein-2 Is Involved in the Dynamics of Microtubules", *J. Biol. Chem. 275*: 17917, (2000), 17917-17920.
Herbert, M. R., et al., "Dissociations of cerebral cortex, subcortical and cerebral white matter volumes in autistic boys", *Brain 126*: 1182, (2003), 1182-1192.
Hobbs, et al., "Polymorphisms in genes involed in folate metabolism as maternal risk factors for Down syndrome", *Am J Hum Genet 67*: 623, (2000),623-630.
Horch, H W., et al., "Destabilization of cortical dendrites and spines by BDNF", *Neuron 23*: 353, (1999),353-364.
Huang, E J., et al., "Neurotrophins: Roles in neuronal development and function", *Annu Rev Neurosci. 24*: 677, (2001),677-736.
Huttenlocher, P. R., "Dendritic development and mental defect", *Neurology 20*: 381, (1970),381.
Huttenlocher, P. R., "Dendritic development in neocortex of children with mental defect and infantile spasms", *Neurology 24*: 203, (1974),203-210.
Inagaki, Naoyuki , et al., "CRMP-2 induces axons in cultured hippocampal neurons", *Nat. Neurosci. 4*: 781, (2001),781-782.
Irwin, S A., et al., "Abnormal dendritic spine characteristics in the temporal and visual cortices of patients with fragile-X syndrome: a quantitative examination", *Am J Med Genet 98*: 161, (2001),161-167.

(Continued)

*Primary Examiner*—Olga N. Chernyshev
(74) *Attorney, Agent, or Firm*—Fox Rothschild LLP; Gerard P. Norton; Vyacheslav Vasilyev

(57) ABSTRACT

Disclosed are novel materials and screening methods for diagnosing and monitoring cognitive disorders, as well as for identifying compounds for treating such disorders.

11 Claims, No Drawings

OTHER PUBLICATIONS

Jaeken, J., et al., "An infantile austistic syndrome characterised by the presence of succinylpurines in body fluids", *Lancet* 2: 1058, (1984), 1058-1061.

James, S. J., et al., "Abnormal folate metabolism and mutation in the methylenetetrahydrofolate reductase gene may be maternal risk factors for Down syndrome", *Am J Clin Nutr* 70: 495, (1999),495-501.

Jiao, X., et al., "Identification of Target mRNA Substrates for the Murine Deleted in Azoospermia-Like RNA-Binding Protein", *Biol. Reprod.* 66: 475, (2002), 475-485.

Karlin, Samuel, et al., "Classification of mononuclear zinc metal sites in protein structures.", *Proc. Natl. Acad. Sci. USA* 94: 14231, (Dec. 1997), 14231-14236.

Kaufmann, Walter E., et al., "Dendritic Anomalies in Disorders Associated with Mental Retardation", *Cereb. Cortex* 10: 981, (Oct. 2000),981-991.

Lapchak, P A., et al., "Systemic interleukin-1 decreases brain-derived neurotrophic factor messenger RNA expression in the rat hippocampal formation.", *Neuroscience* 53: 297, (1993),297-301.

Lee, Alan, et al., "Control of dendritic development by the *Drosophila* fragile X-related gene involves the small GTPase Rac1", *Development* 130: 5543, (2003),5543-5552.

Lesch, M, et al., "A familial disorder of uric acid metabolism and central nervous system function", *Am. J. Med.* 36: 561, (Apr. 1964),561-570.

Lom, Barbara, et al., "Brain-Derived Neurotrophic Factor Differentially Regulates Retinal Ganglion Cell Dendritic and Axonal Arborization in Vivo", *J. Neurosci.* 19: 9928, (1999),9928-9938.

Marin-Padilla, M., "Pyramidal cell abnormalities in the motor cortex of a child with Down's syndrome", *J. Comp. Neurol.* 167: 63, (1976),63-75.

McAllister, A K., "Neurotrophin regulation of cortical dendritic growth requires activity.", *Neuron* 17: 1057, (1996), 1057-1064.

McAllister, A K., "Neurotrophins regulate of dendritic growth in developing visual cortex.", *Neuron* 15: 791, (1995), 791-803.

McAllister, A.K., et al., "Opposing roles for endogenous BDNF and NT-3 in regulating cortical dendritic growth.", *Neuron* 18: 767, (1997),767-778.

Messahel, Souad, et al., "Abnormalities In Urinary Pterin Levels In Rett Syndrome", *Eur. J. Paediatr. Neurol.* 4: 211, (2000),211-217.

Narisawa-Saito, M, et al., "Differential regulation of hippocampal neurotrophins during aging in rats.", *J. Neurochem.* 67: 1124, (1996),1124-1131.

Nimchinsky, Esther A., et al., "Abnormal Development of Dendritic Spines in FMR1 Knock-Out Mice", *J. Neurosci.* 21: 5139, (2001),5139-5146.

Ohm, T G., et al., "Transneuronally altered dendritic processing of tangle-free neurons in Alzheimer's disease.", *Acta Neuropathol* 103: 437, (2002),437-443.

Page, T, et al., "De novo purine synthesis is increased in the fibroblasts of purine autism patients", *Adv. Exp. Med. Biol.* 431: 793, (1998),793-796.

Page, T., et al., "Purine metabolism abnormalities in a hyperuricosuric subclass of autism", *Biochim. Biophys. Acta.* 1500: 291, (2000),291-296.

Paletzki, R F., "Cloning and characterization of guanine deaminase from mouse and rat brain.", *Neuroscience* 109: 15, (2002), 15-26.

Prinz, M., et al., "The growth of non-pyramidal neurons in the primary motor cortex on man: a Goldi study", *Histol. Histopathol.* 12: 895, (1997),895-900.

Purpura, D. P., "Dendritic spine dysgenesis and mental retardation", *Science* 186: 1126, (1974),1126-1128.

Purpura, D. P., "Normal and aberrant neuronal development in the cerebral cortex of human fetus and young infant", *UCLA Forum Med Sci.* 18: 141, (1975),141-69.

Puukka, R., et al., "Erythrocyte adenosine deaminase, purine nucleoside phosphorylase and phosphoribosyltransferase activity in patients with Down's syndrome", *Clin. Chim. Acta* 126:275, (1982),275-281.

Puukka, R., et al., "Levels of some purine metabolizing enzymes in lymphocytes from patients with Down's syndrome.", *Biochem Med Metabol Biol* 36: 45, (1986),45-50.

Raemaekers, Tim, et al., "NuSAP, a novel microtubule-associated protein involved in mitotic spindle organization", *J. Cell Biol.* 162: 1017, (2003),1017-1029.

Raymond, G V., et al., "Hippocampus in autism: a Golgi study.", *Acta. Neuropathol.* 91: 117, (1996),117-119.

Rocchigiani, M. S., et al., "Purine and Pyridine Nucleotide metabolism in the Erythrocytes of Patients with Rett Syndrome.", *Neuropediatrics* 26: 288, (1995),288-292.

Rodgers, N D., et al., "Identifying mRNAs Bound by RNA-Binding Proteins Using Affinity Purification and Differential Display", *Methods* 26: 115, (2002),115-122.

Roessler, B J., et al., "Human X-linked phosphoribosylpyrophosphate synthetase superactivity is associated with distinct point mutations in the PRPS1 gene", *J. Biol Chem.* 26826476, (1993), 26476-26481.

Rossiter, B, et al., "Presymptomatic testing for genetic diseases of later life. Pharmacoepidemiological considerations", *Drugs and Aging* 7:117, (1995),117-130.

Schulz, E., et al., "Neurohistological findings in the parietal cortex of children with chromosome aberrations", *J. Hirnforsch* 33: 37, (1992),37-62.

Seegmiller, J E., et al., "Enzyme defect associated with a sex-linked human neurological disorder and excessive purine synthesis", *Science* 155(770): 1682, (Mar. 31, 1967), 1682-1684.

Stone, R L., et al., "A mutation in adenylosuccinate lyase associated with mental retardation and autistic features", *Nat. Genet.* 1: 59, (1992),59-63.

Subramaniam, B., et al., "Neuroanatomy in Rett syndrome: cerebral cortex and posterior fossa", *Neurology* 48: 399, (1997),399-407.

Takashima, S., et al., "Abnormal neuronal development in the visual cortex of the human fetus and infant with Down's syndrome: a quantitative and qualitative Golgi study.", *Brain Res.* 225 1, (1981),1-21.

Takashima, S., et al., "Dendrites, Dementia and the Down Syndrome", *Brain Dev.* 11: 131, (1989),131-133.

Tolwani, R J., et al., "BDNF overexpression increases dendrite complexity in hippocampal dentate gyrus", *Neuroscience* 114: 795, (2002),795-805.

Trifillis, P, et al., "Finding the Right RNA: Identification of cellular mRNA substrates for RNA-binding proteins", *RNA.* 5: 1071, (1999),1071-1082.

Vaillant, A R., et al., "Signaling mechanisms underlying reversible, activity-dependent dendrite formation", *Neuron* 34: 985, (2002),985-998.

Yu, X, et al., "Beta-catenin is critical for dendritic morphogenesis", *Nat. Neurosci.* 6: 1169, (2003),1169-1177.

Yuan, G, et al., "Cloning and Characterization of Human Guanine Deaminase. Purification and Partial Amino Acid Sequence of the Mouse Protein", *J. Biol. Chem.* 274: 8175, (1999),8175-8180.

Zhang, L I., et al., "Electrical activity and development of neural circuits", *Nat Neurosci* 4 (*Suppl*): 1207, (2001), 1207-1214.

Zoghbi, H. Y., et al., "Cerebrospinal Fluid Biogenic Amines and Biopterin in Rett Syndrome", *Ann Neurol* 25: 56, (1989),56-60.

METHODS FOR IDENTIFYING AGONISTS OF CYPIN

CROSS-REFERENCE TO RELATED APPLICATIONS

This application claims priority to U.S. provisional patent application Ser. No. 60/535,512, filed Jan. 12, 2004, U.S. provisional patent application Ser. No. 60/535,533, filed Jan. 12, 2004, U.S. provisional patent application Ser. No. 60/535,534, filed Jan. 12, 2004 and U.S. provisional patent application Ser. No. 60/577,922, filed Jun. 9, 2004, each is herein incorporated by reference.

GOVERNMENT SUPPORT

This invention was made with U.S. Government funds (NSF IBN 0234206). Therefore, the Government may have rights in this invention.

The Sequence Listing in computer readable form is hereby incorporated by reference in its entirety.

FIELD OF THE INVENTION

The present invention generally relates to the structure, function and uses of a protein and fragments thereof, alone and in combination, involved in the regulation of nerve cell activity and morphology, which affects learning and memory disorders.

BACKGROUND OF THE INVENTION

The establishment of dendrite morphology is crucial for normal neuronal communication in the brain. This development includes both the spatial and functional assembly of signal transduction machinery at synaptic sites and precise patterning of dendrites and their branches. Dendrite branching plays an important role in normal brain function. Branching patterns, the relationship between the primary dendrites arising from the cell body and the secondary dendrites arising from primary dendrites, appear to be cell-type specific and play a role in determining how information is received and processed by a neuron. Further, trafficking of proteins during neuronal development and homeostasis affects or is related to dendrite branching. The amount of branches that a dendrite, or input center of a neuron, contains is thought to be directly related to learning and memory. In many learning disorders, such as autism, Rett syndrome, Down syndrome, Fetal Alcohol syndrome and Alzheimer's disease, patients show a reduced number of dendrite branches. These patients also often show alterations in the metabolism, or breakdown, of a class of compounds called purines.

Clues to how neurons regulate their dendritic morphology come from studies of patients with disorders that result in cognitive deficits. Evidence suggests that patients with these disorders have defects in dendrite number and arborization, as well as deficits in purine production, purine metabolism, or pterins, which are important for purine synthesis. Although these studies are mostly correlative, the first evidence for the idea that purine metabolic disorders underlie cognitive defects was from patients with Lesch-Nyhan syndrome (LNS). LNS is an X-linked disorder that involves the absence of hypoxanthine guanine phosphoribosyltransferase (HPRT) (Lesch and Nyhan, *Am. J. Med.* 36:561-70 (1964); Seegmiller et al., *Science* 770:1682-4 (1967); Rossiter and Caskey, *Drugs Aging* 2:117 (1995)). LNS patients suffer from movement disorders, self-injury, and mental retardation. This deficit always results in increased uric acid levels in the urine, reflecting alterations in purine metabolism, and patients often have neurological abnormalities. Besides Lesch-Nyhan syndrome, both dendrite number or branching defects and purine synthesis/metabolism defects are seen in individuals with autism, (Jaeken and Van den Berghe, *Lancet* 2:1058 (1984); Stone et al., *Nat. Genet.* 1:59 (1992); Raymond et al., *Acta. Neropathol.* 91:117 (1996); Page and Coleman, *Adv. Exp. Med. Biol.* 431:793 (1998); Page and Coleman, *Biochim. Biophys. Acta.* 1500:291 (2000); Herbert et al., *Brain* 126:1182 (2003)); Rett syndrome (Belichenko et al., *Neuroreport.* 5:1509 (1994); Belichenko and Dahlstrom, *J. Neurosci. Methods* 57:55 (1995); Rocchigiani et al., *Neuropediatrics* 26:288-92 (1995); Boltshauser et al., *Am. J. Med. Genet. Suppl.* 1:317-21 (1986); Zoghbi et al., *Ann. Neurol.* 25:56 (1989); Subramaniam et al., *Neurology* 48:399 (1997); Messahel et al., *Eur. J. Paediatr. Neurol.* 4:211 (2000); Armstrong, *Brain Dev.* 23 Suppl 1:S72. (2001); Raemaekers et al., *J. Cell Biol.* 162:1017-29 (2003)); Down's syndrome (Fuller et al., *Science* 137:868 (1962); Huttenlocher, *Neurology* 20:381 (1970); Huttenlocher, *Neurology* 24:203 (1974); Purpura, *Science* 186:1126 (1974); Purpura, *UCLA Forum Med. Sci.* 18:141 (1975); Marin-Padilla, *J. Comp. Neurol.* 167:63 (1976); Takashima et al., 1981 *Brain Res.* 225:1 (1981); Puukka et al., *Clin. Chim. Acta.* 126:275 (1982); Puukka et al., *Biochem. Med. Metab. Biol.* 36:45 (1986); Becker et al., *Ann. Neurol.* 20:520 (1986); Takashima et al., *Brain Dev.* 11:131 (1989); Schulz and Scholz, *J. Hirnforsch* 33:37 (1992); Prinz et al., *Histol. Histopathol.* 12:895 (1997); James et al., *Am. J. Clin. Nutr.* 70:495 (1999); Kaufmann and Moser, *Cereb. Cortex.* 10:981 (2000); Hobbs et al., *Am. J. Hum. Genet.* 67:623 (2000)) and Fragile-X syndrome (Berry-Kravis and Huttenlocher, *Ann. Neurol.* 31:22 (1992); Roessler et al., *J. Biol. Chem.* 268:26476 (1993); Irwin et al., *Am. J. Med. Genet.* 98:161 (2001); Nimchinsky et al., *J. Neurosci.* 21:5139 (2001); Galvez et al., *Brain Res.* 971:83 (2003); Garcia-Pavia et al., *Arthritis Rheum.* 48:2036 (2003); Lee et al., *Development* 130:5543 (2003)). There are also reports of decreased dendrite number in patients with Alzheimer's disease (for example Arendt et al., *J. Neurosci.* 17:516 (1997); Ohm et al., *Acta. Neuropathol.* (Berl) 103:437 (2002)).

Thus, although there is no current consensus on how the absence of HPRT affects dendrite number or branching, abnormal dendrite number or branching may underlie the neurological symptoms of LNS and other related disorders. Although purine metabolic defects have not been well characterized in these patients, agents that increase dendrite number and/or branching may act to help these patients with memory. As a result, there is an immediate need for a sensitive assay for early diagnosis of cognitive disorders such as Alzheimer's disease, autism, Rett syndrome, Parkinson's disease, fetal alcohol syndrome, etc, as well as assays for identification of compounds to treat these and other cognitive disorders.

SUMMARY OF THE INVENTION

The present invention fills the foregoing need by providing such assays and materials. The present invention relates to methods of using cypin in assays for diagnosing and monitoring cognitive disorders, such as for example, autism, Lesch-Nyhan syndrome, Rett syndrome, Down syndrome, Fragile-X syndrome, Alzheimer's disease, Parkinson's disease, fetal alcohol syndrome, etc., as well as for identifying compounds to treat these and other cognitive disorders. The present invention exploits Applicant's discoveries regarding cypin, a protein found in nerve cells that controls dendrite development, including the regulation of microtubule assembly, dendrite morphology and dendrite patterning and branching in the brain. Applicant has discovered that cypin acts as a molecular "glue" that cements molecules together into long chains that form the "skeleton" of the dendrite. When humans and animals learn, neurons in the brain become more active, and cypin production increases and dendrite growth increases. In disease states such as Alzeimer's disease, Rhetts syndrome, fetal alcohol syndrome, mental retardation, etc., where there are deficits in memory, there are smaller amounts of branches on neurons. Just as cypin is associated with proper learning and memory, a lack of cypin correlates with learning disabilities and diseases.

Accordingly, one aspect of the present invention is directed to a method for use in the diagnosis of a cognitive disorder in a subject comprising detecting a test amount of a cypin gene product in a sample from the subject; and comparing the test amount with a normal amount of cypin gene product in a control sample, whereby a finding that the test amount is less than the normal amount provides a positive indication in the diagnosis of a cognitive disorder. In some embodiments, the cypin gene product is cypin polypeptide. In other embodiments, the cypin gene product is cypin mRNA or cDNA.

Another aspect of the present invention is directed to a method for use in the prognosis of a cognitive disorder in a subject comprising the steps of: detecting a test amount of a cypin gene product in a sample from the subject; and comparing the test amount with prognostic amounts of the cypin gene product in control samples, whereby a comparison of the test amount with the prognostic amounts provides an indication of the prognosis of cognitive disorder. In some embodiments, the cypin gene product is cypin polypeptide. In other embodiments, the cypin gene product is cypin mRNA or cDNA.

Another aspect of the present invention is directed to a method for use in monitoring the course of a cognitive disorder in a subject comprising the steps of: detecting a first test amount of a cypin gene product in a sample from the subject at a first time; detecting a second test amount of the cypin gene product in a sample from the subject at a second, later time; and comparing the first test amount and the second test amount, whereby an decrease in the amount of the cypin gene product in the second test amount as compared with the first test amount indicates progression of the cognitive disorder, and whereby an increase in the amount of the cypin gene product in the second test amount as compared with the first test amount indicates improvement of the cognitive disorder. In some embodiments, the cypin gene product is cypin polypeptide. In other embodiments, the cypin gene product is cypin mRNA or cDNA.

Another aspect of the present invention is directed to a method for assessing the efficacy of a treatment for a cognitive disorder in a subject comprising the steps of: detecting a first test amount of a cypin gene product in a sample from the subject prior to treatment; detecting a second test amount of the cypin gene product in a sample from the subject after treatment; and comparing the first test amount and the second test amount, whereby an increase in the amount of the cypin gene product in the second test amount as compared with the first test amount indicates that the treatment for the cognitive disorder is efficacious. In some embodiments, the cypin gene product is cypin polypeptide. In other embodiments, the cypin gene product is cypin mRNA or cDNA.

Another aspect of the present invention is directed a method for identifying a compound capable of increasing expression of cypin, comprising: (a) providing a cell capable of expressing cypin; (b) contacting said cell with a candidate agent to be tested; and (c) measuring the level of a cypin gene product, whereby a compound capable of increasing expression of cypin is identified by measurement of an increased level of cypin gene product compared to the level produced in the absence of such compound. In some embodiments, the cypin gene product is cypin polypeptide. In other embodiments, the cypin gene product is cypin mRNA or cDNA.

Another aspect of the present invention is directed a method for identifying a compound capable of decreasing expression of cypin, comprising: (a) providing a cell capable of expressing cypin; (b) contacting said cell with a candidate agent to be tested; and (c) measuring the level of a cypin gene product, whereby a compound capable of decreasing expression of cypin is identified by measurement of a decreased level of cypin gene product compared to the level produced in the absence of such compound. In some embodiments, the cypin gene product is cypin polypeptide. In other embodiments, the cypin gene product is cypin mRNA or cDNA.

Another aspect of the present invention is directed a method for identifying an agonist of cypin comprising: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of an increase in activity as compared to the activity measured in the absence of such agonist. The activity measured can be dendrite formation, dendrite branching, guanine deaminase activity, guanine binding, microtubule formation, tubulin binding, and PDZ domain binding.

Another aspect of the present invention is directed a method for identifying an antagonist of cypin comprising: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of a decrease in activity as compared to the activity measured in the absence of such antagonist. The activity measured can be dendrite formation, dendrite branching, guanine deaminase activity, guanine binding, microtubule formation, tubulin binding, and PDZ domain binding.

Another aspect of the present invention is directed to a method for increasing cypin expression and/or activity in a cell comprising contacting a cell with an agent in an amount effective to increase expression and/or activity of cypin. In some embodiments, the agent is a cypin polypeptide or fragment thereof. In other embodiments, the agent is a compound that increases dendrite formation and/or branching in neurons.

Another aspect of the present invention is directed to a method of regulating dendrite formation and/or branching in a cell comprising contacting a cell capable of forming dendrites with an agent for a time sufficient to increase or decrease dendrite formation and/or branching. In some embodiments, the agent is a cypin polypeptide or fragment thereof.

Another aspect of the present invention is directed to a method of regulating microtubule assembly in a cell comprising contacting a cell with an agent for a time sufficient to induce or inhibit microtubule assembly. In some embodiments, the agent is a cypin polypeptide or fragment thereof.

A method of regulating PSD-95 clustering at postsynaptic sites in a cell comprising contacting a cell with an agent for a time sufficient to increase or decrease PSD-95 clustering. In some embodiments, the agent is a cypin polypeptide or fragment thereof.

Another aspect of the present invention is directed to a fragment of a cypin polypeptide comprising a deletion of one or more domains, including the zinc-binding aminohydrolase domain, the guanine-binding domain, the collapsin response mediator protein (CRMP) homology domain, and the carboxy-terminal PDZ-binding domain. Another aspect is directed to a method of regulating endogenous cypin activity in a cell comprising contacting a cell with a cypin fragment for a time sufficient to increase or decrease endogenous cypin activity in a cell. Other aspects are directed to nucleic acid molecules encoding cypin fragments, vectors comprising these nucleic acid molecules, host cells comprising these vectors, and methods of producing cypin fragments by culturing these host cells. Still another aspect is directed to antibodies that specifically bind to epitopes located in these cypin fragments. Still another aspect is directed to methods of detecting cypin or a fragment thereof in a biological sample comprising contacting a biological sample with these antibodies. Still another aspect is directed to a kit for detecting cypin or a fragment thereof in a biological sample comprising these antibodies.

These and other aspects of the present invention will be better appreciated by reference to the Detailed Description.

DETAILED DESCRIPTION

The present invention results from the unexpected discovery of several physiological functions for cypin that has not heretofore been described. This discovery has permitted the development of methods of using cypin in assays for diagnosing and monitoring cognitive disorders, as well as assays for identifying compounds to treat these disorders.

Methods for Diagnosing, Prognosing, and Monitoring the Progress of Cognitive Disorders Introduction The present invention provides methods for diagnosing cognitive disorders by detecting decreased levels of cypin. "Diagnostic" or "diagnosing" means identifying the presence or absence of a pathologic condition. Diagnostic methods involve detecting decreased levels of cypin by determining a test amount of cypin gene product (e.g., mRNA, cDNA, or polypeptide, including fragments thereof) in a biological sample from a subject (human or nonhuman mammal), and comparing the test amount with a normal amount or range (i.e., an amount or range from an individual(s) known not to suffer from a cognitive disorder) for the cypin gene product. While a particular diagnostic method may not provide a definitive diagnosis of a cognitive disorder, it suffices if the method provides a positive indication that aids in diagnosis.

The present invention also provides methods for prognosing a cognitive disorder by detecting levels of cypin. "Prognostic" or "prognosing" means predicting the probable development and/or severity of a pathologic condition. Prognostic methods involve determining the test amount of a cypin gene product in a biological sample from a subject, and comparing the test amount to a prognostic amount or range (i.e., an amount or range from individuals with varying severities of a cognitive disorder) for the cypin gene product. Various amounts of the cypin gene product in a test sample are consistent with certain prognoses for cognitive disorders. The detection of an amount of cypin gene product at a particular prognostic level provides a prognosis for the subject.

The present invention also provides methods for monitoring the course of a cognitive disorder by detecting levels of cypin. Monitoring methods involve determining the test amounts of a cypin gene product in biological samples taken from a subject at a first and second time, and comparing the amounts. A change in amount of cypin gene product between the first and second time indicates a change in the course of a cognitive disorder, with an increase in amount indicating improvement of the disorder, and a decrease in amount indicating progression of the disorder. Such monitoring assays are also useful for evaluating the efficacy of a particular therapeutic intervention (e.g., disease attenuation vs. reversal) in patients being treated for a cognitive disorder.

Biological Sample Collection

Expression of cypin can be detected in a variety of biological samples, including cells (e.g., whole cells, cell fractions, and cell extracts) and tissues. Biological samples also include sections of tissue such as biopsies and frozen sections taken for histological purposes. Preferred biological samples include blood samples, nasal biopsies, brain tissue, and spinal fluid.

Normal, Diagnostic, and Prognostic Values

In the diagnostic and prognostic assays of the present invention, the cypin gene product is detected and quantified to yield a test amount. The test amount is then compared to a normal amount or range. An amount above the normal amount or range (e.g., a 30% or greater increase (with $p<0.01$), or a 100% or greater increase (with $p<0.05$)) is a positive sign in the diagnosis of a cognitive disorder. Particular methods of detection and quantitation of cypin gene products are described below.

Normal amounts or baseline levels of cypin gene products can be determined for any particular sample type and population. Generally, baseline (normal) levels of cypin protein or mRNA are determined by measuring the amount of cypin protein or mRNA in a biological sample type from normal (i.e., healthy) subjects. Alternatively, normal values of cypin gene product can be determined by measuring the amount in healthy cells or tissues taken from the same subject from which the diseased (or possibly diseased) test cells or tissues were taken. The amount of cypin gene product (either the normal amount or the test amount) can be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of cypin gene product because relative values are sufficient for many applications of these methods. It will also be appreciated that in addition to the quantity or abundance of cypin gene products, variant or abnormal cypin gene products or their expression patterns (e.g., mutated transcripts, truncated polypeptides) may be identified by comparison to normal gene products and expression patterns.

Assays for Cypin Gene Products

The diagnostic, prognostic, and monitoring assays of the present invention involve detecting and quantifying cypin gene products in biological samples. Cypin gene products include, for example, cypin mRNA and cypin polypeptide (or fragments thereof), and both can be measured using methods well known to those skilled in the art.

For example, cypin mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention are based on the nucleic acid sequence of cypin and are well known in the art.

Alternatively, cypin mRNA can be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified cypin gene products (e.g., mRNA or cDNA) may be readily designed and produced without undue experimentation by those of skill in the art based on the nucleic acid sequence of cypin. Amplified cypin gene products may be directly analyzed, e.g., by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that whichever amplification method is used, a variety of quantitative methods known in the art (e.g., quantitative PCR) may be used if quantitation of cypin gene products is desired.

Cypin polypeptides (or fragments thereof) can be detected and quantified using various well-known enzymatic and immunological assays. Enzymatic assays refer to assays that utilize cypin substrates to detect guanine deaminase activity. Guanine deaminase activity can assayed by following the conversion of guanine to xanthine as described in, e.g., Yuan et al., *J. Biol. Chem.* 274:8175 (1999) and Paletzki, *Neuroscience* 109:15 (2002). Immunological assays refer to assays that utilize an antibody (e.g., polyclonal, monoclonal, chimeric, humanized, scFv, and fragments thereof) that specifically binds to a cypin polypeptide (or a fragment thereof). A number of well-established immunological assays suitable for the practice of the present invention are known, and include enzyme linked immunosorbent assay (ELISA), radioimmunoassay (RIA), immunoprecipitation, immunocytostaining, immunodiffusion, and Western blotting.

The anti-cypin antibodies to be used in the methods of the present invention can be produced by methods well known to those skilled in the art. For example, monoclonal antibodies to cypin can be produced by generation of hybridomas in accordance with known methods. Hybridomas formed in this manner are then screened using standard methods, such as ELISA, to identify one or more hybridomas that produce an antibody that specifically binds to cypin, or a fragment thereof. Full-length cypin may be used as the immunogen, or, alternatively, antigenic peptide fragments of cypin may be used. Fragments of particular interest missing various cypin domains or encompassing various domains are described below. Such fragments can be used in assays, e.g., ELISAs, to identify antibodies that bind epitopes in specific domains of cypin, including the the zinc-binding aminohydrolase domain, guanine binding domain, the collapsin response mediator protein (CRMP) homology domain and the carboxy-terminal PDZ-binding domain (see Akum et al., *Nature Neurosci.* 7:145 (2004).

As an alternative to preparing monoclonal antibody-secreting hybridomas, a monoclonal antibody to cypin, or a fragment thereof, may be identified and isolated by screening a recombinant combinatorial immunoglobulin library (e.g., an antibody phage display library) to thereby isolate immunoglobulin library members that bind to cypin, or a fragment thereof. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with cypin (preferably mammalian; more preferably human) or an antigenic fragment thereof. The antibody titer in the immunized subject may be monitored over time by standard techniques, such as with ELISA, using immobilized marker protein. If desired, the antibody molecules directed against cypin may be isolated from the subject or culture media and further purified by well-known techniques, such as protein A chromatography, to obtain an IgG fraction, or by affinity chromatography, as described in Firestein et al., *Neuron* 24:659 (1999).

Fragments of antibodies to cypin may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to cypin, comprising both human and nonhuman portions, may be produced using standard recombinant DNA techniques. Humanized antibodies to cypin may also be produced using transgenic mice that are incapable of expressing endogenous immunoglobulin heavy and light chain genes, but which can express human heavy and light chain genes.

In the immunological assays of the present invention, the cypin polypeptide is typically detected directly (i.e., the anti-cypin antibody is labeled) or indirectly (i.e., a secondary antibody that recognizes the anti-cypin antibody is labeled) using a detectable label. The particular label or detectable group used in the assay is usually not critical, as long as it does not significantly interfere with the specific binding of the antibodies used in the assay.

The immunological assays of the present invention may be competitive or noncompetitive. In competitive assays, the amount of cypin in a sample is measured indirectly by measuring the amount of added. (exogenous) cypin displaced from a capture agent (i.e., an anti-cypin antibody) by the cypin in the sample. In noncompetitive assays, the amount of cypin in a sample is directly measured. In a preferred noncompetitive "sandwich" assay, the capture agent (e.g., a first anti-cypin antibody) is bound directly to a solid support (e.g., membrane, microtiter plate, test tube, dipistick, glass or plastic bead) where it is immobilized. The immobilized agent then captures any cypin polypeptide present in the sample. The immobilized cypin can then be detected using a second labeled anti-cypin antibody. Alternatively, the second anti-cypin antibody can be detected using a labeled secondary antibody that recognizes the second anti-cypin antibody.

Kits

The methods and reagents of the present invention can be conveniently packaged in kit form. Such kits can be used in the diagnostic, prognostic, and monitoring methods described above. For example, such kits may include an anti-cypin antibody (or fragment thereof) and a control antibody that does not react with cypin, as well as instructional materials for using the kits to detect cypin. Such kits may also include a substantially isolated cypin polypeptide (or fragment thereof) comprising an epitope which is specifically immunoreactive with at least one anti-cypin antibody, which may be bound to a solid support (e.g., slides, chips, membranes, beads, microtiter plates, etc.). Further, such kits may include means for detecting the binding of the anti-cypin antibody (or fragment thereof) to cypin in a biological sample (e.g., the anti-cypin antibody may be conjugated to a fluorescent compound such as fluorescein or rhodamine, or a second labeled antibody may be included that binds to anti-cypin). The kits may also include hybridization and wash solutions, buffers, salts, nuclease-free water, containers, vials, reaction tubes, cover slips, various signal-detecting, signal-producing, signal-enhancing, and signal-preserving reagents, and the like compatible with the use of the kits to detect cypin.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

Screening Methods for Identifying Compounds that Increase Cypin Expression and/or Activity Introduction As described below, increased cypin expression and activity in neurons correlates with dendrite number and branching, whereas decreased cypin levels correlates with decreased dendrite number and branching. This regulation of dendrites is due in part to cypin's guanine deaminase activity. Accordingly, the present invention provides methods (also referred to herein as "screening assays") for identifying novel compounds that increase the expression or activity of cypin. In one embodiment, cells that are capable of expressing cypin (preferably neurons) are contacted with a test compound to determine whether the compound increases expression of a cypin gene product (e.g., mRNA or polypeptide). Changes in cypin gene expression can be determined by any method known in the art or described above. The changes in expression can be correlated with morphological changes associated with cypin activity, such as dendrite number and branching. Compounds identified that increase cypin expression (either mRNA or polypeptide) are candidates as drugs for the prophylactic and therapeutic treatment of cognitive disorders.

Alternatively, compounds can be identified that increase the activity of cypin. Such compounds are considered agonists of cypin. Generally, a method for identifying an agonist of cypin comprises: (a) providing a sample comprising a cypin polypeptide or fragment thereof; (b) contacting said sample with a candidate agent to be tested for cypin agonistic activity; and (c) measuring the activity of cypin polypeptide or fragment thereof, whereby a cypin agonist is identified by measurement of an increase in activity as compared to the activity measured in the absence of such agonist. Cypin (or a fragment thereof) can be contacted with a test compound to determine whether the compound increases the activity of cypin (as compared to an untreated sample of cypin). Compounds identified that increase cypin activity can then be tested in in vitro and in vivo models of cognitive disorders, such as the Rett syndrome mouse (MeCP2 knockout mouse), the Lesch-Nyhan Disease mouse (HPRT knockout mouse), the Alzheimers Disease rat model, etc.

Generally, a plurality of assays can be run in parallel with different agent concentrations to obtain a differential response to the various concentrations. Typically, one of these concentrations serves as a negative control, i.e., at zero concentration or below the level of detection. In addition, candidate agents can be contacted with a non-cypin molecule as a control for target specificity. Although the screening methods are generally used as an assay to identify previously unknown molecules that can act as a therapeutic agent, the method can also be used to confirm and standardize the desired activity of known cypin agonists or to optimize the structure and/or activity of a known cypin agonist during, e.g., molecular evolution procedures.

The screening assays used to identify cypin agonists can be either cell-based or cell-free assays. Cell-free assays are preferred because they are easily adaptable to high-throughput screening procedures (e.g., BIACORE™ (Biacore International AB, Uppsala, Sweden), BRET (bioluminescence resonance energy transfer), FRET (fluorescence resonance energy transfer), ELISA, spectrophotometric tubulin binding and tubulin polymerization assays, etc.). For example, samples containing purified or partially purified cypin can be contacted with one of a plurality of test compounds, and the activity of cypin in each of the treated samples can be compared to the activity of cypin in untreated samples or in samples contacted with different test compounds to determine whether any of the test compounds provides a substantially increased level of cypin activity, thereby identifying an agonist of cypin activity.

Any acitivity associated with cypin (or a fragment thereof) can be assayed in the screening methods. Such cypin activity includes, but is not limited to, dendrite formation, dendrite branching, guanine deaminase activity, guanine binding, microtubule formation, tubulin binding, and binding to proteins containing PDZ domains (e.g., PSD-95). For binding activities, a reaction mixture is generally first prepared containing cypin (or a binding domain thereof) and its binding partner (e.g., tubulin, PDZ, etc.) under conditions and for a time sufficient to allow the two to interact and bind, thus forming a complex. The increased rate of formation of a complex in the reaction mixture containing the test compound compared to the control reaction indicates that the compound is an agonist of the cypin. Compounds that are so identified can then be further evaluated for their ability to increase dendritic formation and/or branching in cell-based assays.

The screenings assays described herein can also be used to identify compounds that decrease activity of cypin (i.e., antagonists). For example, samples containing purified or partially purified cypin can be contacted with one of a plurality of test compounds, and the activity of cypin in each of the treated samples can be compared to the activity of cypin in untreated samples or in samples contacted with different test compounds to determine whether any of the test compounds provides a substantially decreased level of cypin activity, thereby indicating an antagonist of cypin activity.

Compounds identified that increase or decrease cypin expression and/or activity can be tested in cell-based assays to determine their effect on cell morphology. Preferably, the compounds are contacted with cells capable of forming dendrites (such as neurons) to determine the effect on dendrite formation and/or branching.

Sources of Cypin

Any cypin can be used in the methods of the present invention. The amino acid sequences of various cypin polypeptides are publicly available from Genbank and include human (Acc. No. NP_004284; SEQ ID NO: 1), orangutan (Acc. No. CAH91101; SEQ ID NO: 3); rat (Acc. No. AAF63337; SEQ ID NO: 5) and mouse (Acc. No. NP_034396; SEQ ID NO: 7). The cypin can be isolated from natural sources, produced by recombinant methods, or produced through in vitro protein synthesis. Thus, the present invention does not require that cypin be naturally occurring. Analogs of cypin that are functionally equivalent in terms of possessing any one or more of above-described activities may also be used. Thus, representative analogs include fragments of cypin that possess, e.g., dendrite formation activity, dendrite branching activity, guanine deaminase activity, microtubule formation activity, tubulin binding activity and/or PDZ domain binding activity.

Other than fragments of cypin, analogs may differ from the naturally occurring protein in terms of one or more amino acid substitutions, deletions, additions, or rearrangements. For example, functionally equivalent amino acid residues may be substituted for residues within the sequence resulting in a change of sequence. Such substitutes may be selected from other members of the class to which the amino acid belongs: e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic acid and glutamic acid.

Cypin can be purified or partially purified from various tissues (preferably mammalian; more preferably human), including brain, bone, cervix, colon, eye, kidney, liver, lung, mammary gland, muscle, ovary, pancreas, placenta, small intestine, stomach, tongue, testis, uterus and erythrocytes, using known purification processes such as gel filtration and ion exchange chromatography. Purification may also include affinity chromatography with agents known to bind cypin (e.g., anti-cypin antibodies, tubulin, PSD-95, etc.). These purification processes may also be used to purify cypin (or fragments thereof) from recombinant sources.

Once purified, the cleavage of the cypin into fragments of amino acid residues can be achieved using proteolytic enzymes such as thrombin or clostridiopeptidase B (clostripain). The exact time required for proteolysis varies with each cypin and markedly depends upon the batch of clostripain used. Therefore, the optimum time for a single cleavage must be determined for each combination of clostripain batch and cypin used. The cypin fragments resulting from either thrombin or clostripain proteolysis may be further cleaved by digestion with trypsin, which cleaves on the carboxy terminus of lysine or arginine residues.

The sequence of cypin derived from proteolytic digestion may be identified using the Edman degradation method of protein sequencing. In addition, sequence analysis of cypin may be accelerated by using an automated liquid phase amino acid sequenator, thereby allowing for the analysis of picomolar quantities of cypin containing up to 50 amino acid residues in length.

The production of cypin can also be achieved by recombinant DNA technology. Nucleic acid sequences encoding cypin (or fragments thereof) can be produced using methods well known in the art, including chemical synthesis and PCR. Nucleic acid sequences encoding cypin polypeptides from various species as set forth in SEQ ID NOs: 1, 3, 5 and 7 are publicly available from Genbank and include human (Acc. No. NM_004293; SEQ ID NO: 2), orangutan (Acc. No. CR858902; SEQ ID NO: 4); rat (Acc. No. AF245172; SEQ ID NO: 6) and mouse (Acc. No. NM_010266; SEQ ID NO: 8). Due to the degeneracy of the genetic code, many different nucleotide sequences can encode the cypin polypetides of SEQ ID NOs: 1, 3, 5 and 7. The codons can be selected for optimal expression in prokaryotic or eukaryotic systems. Homologous sequences (both paralogues and orthologues) can also be used so long as they retain the structure and/or activity of cypin. Methods for identifying homologous nucleic acid and amino acid sequences are well known in the art and include both hybridization-based and bioinformatics-based approaches (see Baxevanis and Ouellette, *Bioinformatics, A Practical Guide to the Analysis of Genes and Proteins* (2001)).

Recombinant DNA technology is particularly suited to the production of active fragments of cypin. Applicant has identified several cypin fragments of interest that can be used in the methods of the present invention. By "fragment" is meant any portion of cypin smaller than the full-length protein, whether the deleted portion is at an end or in the middle of cypin. Such fragments find utility as antigens for antibody production, targets for screening assays, therapeutical compounds, and regulators (e.g., activators and inhibitors) of endogenous cypin polypeptide activity.

One such cypin fragment comprises a deletion of its zinc-binding aminohydrolase domain (e.g., a deletion amino acids 76-84 of SEQ ID NOs; 1, 3, 5 and 7; a deletion of amino acids 1-220 of SEQ ID NOs: 1, 3, 5 and 7). Another cypin fragment comprises a deletion of its guanine-binding domain (e.g., a deletion of amino acids 233-250 of SEQ ID NOs: 1, 3, 5 and 7). Another cypin fragment comprises a deletion of its collapsin response mediator protein (CRMP) homology domain (e.g., a deletion of amino acids 350-403 of SEQ ID NOs: 1, 3, 5 and 7). Another cypin fragment comprises a deletion of its carboxy-terminal PDZ-binding domain (e.g., a deletion of amino acids 451-454 of SEQ ID NOs: 1, 3, 5 and 7). Another cypin fragment comprises a deletion of its zinc-binding aminohydrolase domain and its guanine-binding domain (e.g., a deletion of amino acids 1-349 of SEQ ID NOs: 1, 3, 5 and 7). Another cypin fragment comprises a deletion of its guanine-binding domain and its collapsin response mediator protein (CRMP) homology domain (e.g., a deletion of amino acids 101-450 of SEQ ID NOs: 1, 3, 5 and 7). Another cypin fragment comprises a deletion of its guanine-binding domain, its collapsin response mediator protein (CRMP) homology domain, and its carboxy-terminal PDZ-binding domain (e.g., a deletion of amino acids 221-454 of SEQ ID NOs: 1, 3, 5 and 7)

The nucleic acid sequences encoding these and other cypin fragments can be produced using methods known in the art, such as chemical synthesis, restriction digestion and ligation, deletion and site-directed mutagenesis, and PCR using, e.g., the nucleotide sequences set forth in SEQ ID NOs: 2, 4, 6 and 8 as templates. Again, due to the degeneracy of the genetic code, many different nucleotide sequences can serve as templates for and encode these cypin fragments. If not present naturally, an initiator methionine in proper Kozak context can be provided for efficient translation of the cypin fragments.

Insertion of a nucleic acid sequence encoding a cypin polypeptide (or fragment thereof) into a vector is readily accomplished when the termini of the nucleic acid sequence and the vector comprise compatible restriction sites. If this cannot be done, it may be necessary to modify the termini of the nucleic acid and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated by the use of PCR. The cleaved vector and the DNA fragments may also be modified if required by homopolymeric tailing.

Recombinant expression vectors for expression of cypin (or fragments thereof) are typically self-replicating DNA constructs comprising a nucleic acid sequence encoding a cypin polypeptide (or fragment thereof) operably linked to a suitable genetic control element that is capable of regulating expression of the nucleic acids in a compatible hosts cell. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Suitable prokaryotic promoters include the β-lactamase and lactose promoter systems, the tryptophan (trp) promoter system, the lambda $P_L$ promoter system and the tac promoter. Numerous expression vectors containing such control sequences are known in the art and available commercially. Suitable eukaryotic promoters include the cytomegalovirus (CMV) promoter, the SV40 early promoter region, the promoter contained in the 3' long terminal repeat of Rous sarcoma virus (RSV), the herpes TK promoter, the adenoviral promoter of an early or late (E1A, MLP, etc.) gene, the regulatory sequences of the metallothionein (MT) and phosphoglycerokinase (PGK) genes, as well as cypin promoters themselves.

Suitable host cells for expressing a nucleic acid sequence encoding a cypin polypeptide (or fragment thereof) include prokaryotes and lower eukaryotes. Suitable prokaryotes include both gram negative and positive organisms, e.g., *E. coli* and *B. subtilis, S. typhimurium*, or any bacterial strain capable of expressing heterologous proteins. Suitable lower eukaryotes include yeast strains such *S. cerevisiae, S. pombe, Kluyveromyces* strains, *Candida*, or any yeast strain capable of expressing heterologous proteins. If the protein is made in yeast or bacteria, it may be necessary to modify the protein produced therein, for example by phosphorylation or glycosylation of the appropriate sites, or by introduction of the targeting sequences, in order to obtain a functional protein. Such covalent attachments may be accomplished using known chemical or enzymatic methods.

The host cell is preferably a higher eukaryote cell line. Suitable higher eukaryote cell lines include both primary and established cell lines from animal cells, both of non-mammalian origin, e.g., insect cells and birds, and of mammalian origin, e.g., human, primates, and rodents.

Higher eukaryotic tissue culture cells are preferred hosts for the recombinant production of a cypin polypeptide (or fragment thereof). Although any higher eukaryotic tissue culture cell line might be used, including insect baculovirus expression systems, mammalian cells are preferred. Suitable mammalian cell lines include HeLa cells, Chinese hamster ovary (CHO) cells, baby rat kidney (BRK) cells, baby hamster kidney (BHK) cells, African green monkey kidney (COS and CV-1) cells, human embryonic kidney (HEK 293) cells, A431 cells, Colo205 cells, 3T3 cells, mouse L cells, HL-60 cells, U937 cells, HaK cells, Jurkat cells, Madin Darby Canine Kidney (MCDK) cells, and PC12 cells. Preferably, the cell line is capable of dendrite formation and/or branching, such as PC12 cells treated with NGF. Primary cultures of rat and mouse meurons are most preferable.

Methods for the transformation or transfection of such cells are well known in the art and include electroporation, calcium phosphate co-precipitation, protoplast or spheroplast fusion, lipofection, DEAE-dextran-mediated transfection, biolistics, and viral infection. The transfected expression vector can be maintained transiently in the cell. Alternatively, if the expression vector contains a selectable marker, cells can be selected in which the vector has stably integrated into the genome by culturing the transfected cells in the appropriate antibiotic or drug. Sutiable dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin, and the bacterial xanthine-guanine phosphoribosyl transferase gene (also referred to as the gpt gene) which confers the ability to grow in the presence of mycophenolic acid.

In order to facilitate purification, cypin (or fragments thereof) may be recombinantly expressed as fusions with proteins such as maltose-binding protein (MBP), glutathione-S-transferase (GST), thioredoxin (TRX) or $His_6$. Kits for expression and purification of such fusion proteins are commercially available from New England BioLabs (Beverly, Mass.), Pharmacia (Piscataway, N.J.), and Invitrogen (Carlsbad, Calif.). Cypin can also be tagged with a small epitope, such as FLAG, HA, T7 or au5, and subsequently identified or purified using a specific antibody to the epitope. One such epitope is the FLAG epitope, which is commercially available from Eastman Kodak (New Haven, Conn.). Cypin (or fragments thereof) can also be fused to marker proteins, such as β-galactosidase, green fluorescent protein and variants (yello, cyan), DsRed proteins, monomeric red fluorescent protein, and luciferase to facilitate localization in situ. Fusions to fluorescent and luminescent proteins also facilitate the use of high-throughput screening assays, such as BRET and FRET, described above.

Cypin (or fragments thereof) may also be produced by known conventional chemical synthesis. Methods for chemically synthesizing polypeptides are well known to those skilled in the art. Such chemically synthetic cypin should possess biological properties in common with the naturally produced form, and thus can be employed as a biologically active or immunological substitute for natural cypin.

Sources of Test Compounds

Any candidate agent or compound can be screened in the above-described methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to, peptides, saccharides, fatty acids, steroids, purines, pyrimidines, and various derivatives, structural analogs and combinations thereof. Preferably, the candidate agent is a small organic compound capable of crossing the blood brain barrier, such as a benzodiazapene, a biphenyl, or heterocycles in general.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Any compounds identified can serve as conventional "lead compounds" or can be used as the actual therapeutics for treatment of cognitive disorders.

Methods of Treatment

Introduction

The present invention provides both prophylactic and therapeutic methods for the treatment of cognitive disorders by increasing expression and/or activity of cypin. The methods generally involve contacting cells (either in vitro, in vivo, or ex vivo) with an agent in an amount effective to increase expression and/or activity of cypin. Any cell can be contacted, preferably a cell capable of forming primary and/or secondary dendrites, such as neurons. When cells are contacted in vivo or ex vivo, the methods can also be described as "methods for treating a subject". Any subject that suffers from a cognitive disorder can be treated, preferably mammalian, more preferably human.

Administration

In one embodiment, the agent contacted is a cypin polypeptide (or fragment thereof). For example, attaching a cypin polypeptide (or a fragment thereof) to cell permeable peptides, such as antennapaedia or Tat will allow cypin to cross the cell membrane. "Contacting with a cypin polypeptide (or fragment thereof)" can also be accomplished by transfection of a recombinant expression vector comprising a nucleic acid molecule encoding a cypin polypeptide (or fragment thereof) using any of the methods described above or, e.g., by inhalation of a liposome formulation containing such a vector through the the nasal cavity for direct access to the brain.

In another embodiment, the agent is a compound that activates dendrite formation and/or branching, such as KCl or various neurotrphins, such as NGF or BDNF. Alternatively, the agent is a compound that increases the intracellular stores of guanine, be it guanine itself, a soluble guanine analog, such as acetoxyacetyl- or methoxyacetylguanine, or some other compound.

In a further embodiment, the agent is any one or more of the novel compounds identified by the screening methods described above that increases expression and/or activity of cypin.

All such compounds described herein can be administered in vivo in the form of a pharmaceutical composition for the treatment of a cognitive disorder. The pharmaceutical compositions may be administered by any number of routes, including, but not limited to, oral, nasal, rectal, topical, sublingual, intravenous, intramuscular, intraarterial, intramedullary, intrathecal, intraventricular, intraperitoneal, intraarticular, or transdermal routes. In addition to the active ingredients, the pharmaceutical compositions may contain pharmaceutically acceptable carriers comprising excipients, coatings, and auxiliaries known in the art.

For preparing pharmaceutical compositions from the compounds described above, inert, pharmaceutically acceptable carriers can be either solid or liquid. Solid form preparations include powders, tablets, dispersible granules, capsules, cachets, suppositories and liposomes. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds may also be deliverable transdermally. The transdermal compositions can take the form of creams, lotions, aerosols and/or emulsions and can be included in a transdermal patch of the matrix or reservoir type as are conventional in the art for this purpose.

The compounds may also be delivered subcutaneously. Preferably the compounds are administered orally or nasally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compound and/or the pharmaceutically acceptable salts thereof will be regulated according to the judgment of the attending clinician considering such factors as age, condition and size of the patient, the severity of the symptoms being treated, and the toxicity profile of the compound.

For any compound, the therapeutically effective dose can be estimated initially either in cell culture or in animal models. The therapeutically effective dose refers to the amount of active ingredient that ameliorates the condition or its symptoms. Therapeutic efficacy and toxicity in cell cultures or animal models may be determined by standard pharmaceutical procedures (e.g., $ED_{50}$: the dose therapeutically effective in 50% of the population; $LD_{50}$: the dose lethal to 50% of the population). The dose ratio between therapeutic and toxic effects is the therapeutic index, and can be expressed as the ratio $ED_{50}/LD_{50}$. Pharmaceutical compositions that exhibit large therapeutic indexes are preferred.

The data obtained from cell culture and animal models can then be used to formulate a range of dosage for the compound for use in mammals, preferably humans. The dosage of such a compound preferably lies within a range of concentrations that include the $ED_{50}$ with little to no toxicity. The dosage may vary within this range depending upon the composition form employed and the administration route utilized. A typical recommended daily dosage regimen will generally range from about 0.001 mg/day to about 1000 mg/day, preferably from about 0.1 to 300 mg/day, more preferably from about 1 mg/day to 50 mg/day, in two to four divided doses.

Specific embodiments according to the methods of the present invention will now be described in the following examples. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

EXAMPLES

Example 1

Cypin immunolocalization in cultured hippocampal neurons

Cypin is a recently identified guanine deaminase that perturbs post-synaptic trafficking of (membrane associated guanylate knase) MAGUK proteins, such as PSD-95 and SAP-102 (Firestein et al., Neuron 24:659 (1999)), which play a role in the maturation of excitatory synapses (El-Hussein, et al., Science 290:364 (2000)). Cypin interacts with the first and second PDZ domains of PSD-95 via a carboxy-terminal canonical PDZ-binding domain (SSSV) (Firestein et al., Neuron 24:659 (1999)).

To establish cypin's role in neuronal development, rat hippocampal neurons were cultured and immunohistochemistry performed using an antibody that was raised against cypin (Id.). This antibody was shown to be specific for cypin protein. Cypin was expressed early in culture and continued to be expressed as neurons matured (Id. ). Cultures were also co-stained using an antibody raised against MAP2, a marker of dendrites, to determine the localization of cypin protein. Cypin was expressed in developing dendrites and increased its expression in axons as the neurons matured (Id.). Similar localization was shown in neurons in the adult cortex, hippocampus, striatum, and superior colliculus (Id.).

Example 2

Regions of cypin involved in guanine deaminase activity

Cypin shares a nine amino acid sequence (PGX(V/I)DXH (T/V/I)H), located at amino acid residues 76-84, found in other aminohydrolases and amidohydrolases, including 28 enzymes from 20 different species (Yuan. et al., *J. Biol. Chem.* 274:8175 (1999); Karlin et al., *Proc. Nat'l. Acad. Sci. USA*, 94:14231 (1997); Akum et al., *Nature Neurosci.* 7:145 (2004)). This short motif is believed to be important for zinc binding. Cypin also contains a region at amino acids 350-403 highly homologous to the collapsin-response mediator protein (CRMP) family and the *C. elegans* unc-33 gene (Akum et al., *Nature Neurosci.* 7:145 (2004)). Recent evidence suggests that CRMP-2 directly binds to tubulin heterodimers and promotes microtubule assembly (Gu et al., *J. Biol. Chem* 275:17917 (2000); Fukata et al., *Nat. Cell Biol.* 4:583 (2002)) and that overexpression of CRMP-2 induces multiple axon formation (Inagaki et al., *Nat. Neurosci.* 4:781 (2001)). Cypin also contains a canonical PDZ-binding sequence (SSSV) at its carboxyl terminus (amino acids 451-454) (Akum et al., *Nature Neurosci.* 7:145 (2004)).

To define which of these domains play a role in guanine deaminase activity, cDNAs encoding N-terminal green fluorescent protein (GFP) fusions of deletion mutants of rat cypin (cypin-GFP) were constructed using site-directed mutogenesis or PCR (Id.). COS-7 cells were then transfected with the cDNAs and assayed for guanine deaminase activity using a colorimetric assay as described in Paletzki, *Neuroscience* 109:15 (2002). The deletion of either the zinc-binding domain (amino acids 76-84) (cypinΔ(76-84)-GFP) or the CRMP-homology domain (amino acids 350-403) (cypinΔ(350-403)-GFP) attenuated guanine deaminase activity (Id.). If the assay was allowed to progress for a longer period of time, cypinΔ(350-403)-GFP did show some activity, suggesting that the CRMP homology domain may play a role in modulating guanine deaminase activity (Id.). Furthermore, both domains are necessary for normal activity since truncation mutants of cypin containing either the first 100 amino acids of cypin fused to the PDZ binding domain (cypin(1-100)SSSV-GFP) or cypin lacking the first 349 amino acids (cypin(350-end)-GFP) did not have guanine deaminase activity (Id.). Deleting the PDZ-binding motif alone (cypin-PDZ-GFP) had no effect on cypin's enzymatic activity (Id.).

Example 3

Cypin increases primary and secondary dendrite number

Cypin is expressed in the dendrites and axons of developing neurons and has high homology to the region of CRMP that binds to tubulin heterodimers. To establish that overexpression of cypin would have an effect on dendrite or axon outgrowth, rat hippocampal neurons were transfected at 10 days in vitro (d.i.v.), a time at which dendrite branching is occurring, with a cDNA encoding rat cypin-GFP, and dendrite number was assessed by co-staining with an antibody raised against MAP-2. Axons were identified as being MAP-2 negative. Overexpression of cypin resulted in a significant increase in both primary and secondary dendrites (Akum et al., *Nature Neurosci.* 7:145 (2004)). There was no effect on axon number (Id.).

To establish that this was not a transient effect of cypin during development, the same experiment was performed with cypin overexpression occurring from 10-17 d.i.v. The number of dendrites was quantitated on d.i.v. 17, when neurons are mature and spines are beginning to form. Consistent with the previous results, cypin-GFP increased primary and secondary dendrite number at this time point. However, the number of primary dendrites at 17 d.i.v. was reduced when compared with that of 12 d.i.v. Furthermore, there appeared to be excessive pruning of secondary dendrites in cultures from 12 d.i.v. to 17 d.i.v. for neurons that overexpressed cypin-PDZ-GFP, a mutant version of cypin that lacks the interaction motif for PSD-95 (Akum, et al., (2004)). Thus, the binding of PSD-95 to cypin has a role in establishing and maintaining stable secondary dendrites.

To determine whether the increase in dendrite number was due to cypin's guanine deaminase activity, rat hippocampal neurons were transfected with cDNAs encoding cypin-PDZ-GFP, cypin$\Delta$(76-84)-GFP, cypin$\Delta$(350-403)-GFP, cypin(1-100)SSSV-GFP, or cypin(350-end)-GFP. The only mutant that retained normal guanine deaminase activity, cypin-PDZ-GFP, increaseed primary and secondary dendrite number at 12 d.i.v. (Id.). The mutants that did not have guanine deaminase activity did not increase dendrite number at 12 or 17 d.i.v. Furthermore, since this mutant cannot bind MAGUK proteins because it lacks its PDZ-binding domain, increase in dendrite number was independent of MAGUK binding. In fact, both cypin$\Delta$(76-84)-GFP and cypin$\Delta$(350-403)-GFP acted as dominant negative proteins, resulting in decreased secondary dendrite number at 12 d.i.v. (Id.). Although not significant, expression of cypin(1-100)SSSV-GFP and cypin(350-end)-GFP appeared to decrease secondary dendrite number (Id.). It is important to note that all constructs express at similar levels ($P>0.05$ by ANOVA followed by Bonferroni Multiple Comparisons Test as compared to cypin-GFP; mean fluorescence intensities are as follows: GFP=880.97 $\pm$103.54; cypin-GFP=701.28$\pm$119.72; cypin$\Delta$(76-84)-GFP=627.23$\pm$121.10; cypin$\Delta$(350-403)-GFP=368.89$\pm$85.83; cypin(1-100)SSSV-GFP=840.19$\pm$144.03; cypin (350-end)-GFP=991.34$\pm$281.61; cypin-PDZ-GFP=705.76$\pm$94.53).

As overexpression of cypin resulted in increased dendrite branching, a novel knockdown strategy based on U1 snRNA (Fortes et al., *Proc. Nat'l. Acad. Sci. USA* 100:8264 (2003) was employed to determine whether attenuation of cypin would result in decreased dendrite in cultured neurons. To knock down cypin in cultured hippocampal neurons, three plasmids were constructed that encode U1 snRNAs where the 5' end is complementary to part of cypin pre-mRNA. Constructs U1-1302 and U1-1338 contained 10 base pair sequences that correspond to the carboxyl terminal end of the coding region of cypin. Construct U1-3'UTR contained 10 bases that correspond to the 5' end of the 3'UTR of cypin. Construct 702 was vector alone. These constructs also expressed GFP off a separate promoter, which served as a marker for expression. Cultured rat hippocampal neurons on 10 d.i.v. were transfected with the constructs and fixed and immunostained for cypin 48 hours post-transfection, at which time the neurons were alive, had dendrites and contained only one axon (as is true at 17 d.i.v.). Constructs U1-1302 and U1-3'UTR attenuated cypin protein expression to levels below or at the threshold of detection in two-thirds of transfected neurons (Akum et al., *Nature Neurosci.* 7:145 (2004)). Construct U1-1338 did not attenuate cypin protein expression (Id.). Further analysis showed that knocking down cypin protein expression significantly decreased dendrite number (Id.). Quantification of fluorescence established a correlation between intensity and dendrite number (Id.).

To address issues that the mutated U1 snRNA had non-specific effects and attenuated expression of other proteins, leading to decreased dendrite number, a plasmid that expressed both cypin-GFP lacking the 3'UTR (U1 recognition site) and U1-3'UTR was constructed. In this circumstance, cypin-GFP served to rescue the phenotype seen when the mutated U1 snRNA specifically knocked down cypin protein expression (Id.). Since dendrite numbers returned to control values, the amount of cypin-GFP that was produced from the U1-3'UTR+cypin plasmid replaced the endogenous cypin that had been knocked out. Together with the overexpression studies, these data suggest that the guanine deaminase activity of cypin plays a role in regulating dendrite branching.

If cypin plays an important role in regulating dendrite morphology as neurons mature, knocking down cypin protein levels should result in decreased primary and secondary dendrites in mature neurons 17 d.i.v. Indeed this was the case. Furthermore, replacing endogenous cypin with cypin-GFP rescued dendrite number as it did at 12 d.i.v. (Id.). Our results indicate that cypin levels regulate dendrite number in mature neurons.

Example 4

Cypin does not merely change global guanine nucleotides

Because cypin is a guanine deaminase, metabolism of guanine by cypin could affect dendrite branching by changing th global levels of guanine nucleotides in neurons. A decrease in GTP in turn could result in decreased activity of small GTPases that are involved in dendrite branching. To address whether cypin regulates dendrite number by this mechanism, dominant negative forms of RhoA, Rac1, and Cdc42 were expressed in rat hippocampal neurons at 10 d.i.v. Expression of these mutants did not change the number of dendrites (Akum et al., *Nature Neurosci.* 7:145 (2004)). Co-expression of these dominant negative proteins with rat cypin-GFP prevented the cypin-mediated increase in primary and secondary dendrite number (Id.). Results with dominant negative GTPases (decreased or no change in branching) gave the opposite result of cypin overexpression (increased branching), which is inconsistent with a model in which cypin causes dendritic branching by simply depleting the global pool of GTP, and thereby decreasing small GTPase activity as a secondary consequence. Furthermore, if cypin globally changed the activity of small GTPases, changes in axon number would be expected (Bito et al., *Neuron* 26:431 (2000); Ellezam et al., *Prog. Brain Res.* 137:371 (2002)), which was not the case. It is possible, however, that cypin may regulate local levels of guanine nucleotides to act through cdc42 and RhoA.

Example 5

Cypin binds directly to tubulin heterodimers

Cypin contains a region of homology to CRMP that binds directly to tubulin heterodimers (Akum et al., *Nature Neurosci.* 7:145 (2004)). To establish that cypin binds to tubulin, affinity chromatography was performed using a GST fusion of rat cypin immobilized on glutathione beads incubated with rat brain extract. The eluate was then assayed for the presence of tubulin. Whereas GST alone did not bind tubulin, immobilized cypin did bind tubulin (Id.). To assess whether this interaction occurs in vivo, rat brain extract was subjected to immunoprecipitation with preimmune serum or polyclonal antibody raised against cypin. Tubulin was found in the cypin immunoprecipitates (Id.). Very little tubulin was present when preimmune serum is used, representing non-specific binding (Id.). Furthermore, no tau was detected in the cypin immunoprecipitates, supporting the idea that cypin binds specifically to tubulin and not all cytoskeletal proteins (Id.). In addition, cypin was found in tubulin immunoprecipitates. This indicates that cypin binds to tubulin in the brain.

Based on homology to CRMP, it was hypothesized that cypin binds directly to tubulin heterodimers. To establish that there is a direct interaction, purified cypin was incubated with tubulin heterodimers and the mixtures subjected to immunoprecipitation with an antibody raised against tubulin. Cypin indeed coimmunoprecipitated with tubulin (Id.). To identify which region of cypin binds to tubulin heterodimers, regions of cypin were purified. As predicted, the first 220 amino acids of cypin (cypin(1-220)), lacking the CRMP region, did not bind to tubulin (Id.). Only when the CRMP region is present (wild-type cypin, cypin(220-end), or cypin(350-end), did cypin co-immunoprecipitate with tubulin heterodimers (Id.). This indicates that the CRMP region mediates the binding of cypin to tubulin heterodimers.

Example 6

Cypin promotes microtubule assembly

As cypin does not increase dendrite number by altering global pools of guanine nucleotides, it was hypothesized that cypin regulates neuronal morphology by promoting microtubule assembly. In fact, it has been shown that CRMP induces multiple axon formation by promoting microtubule assembly. (Inagaki et al., Nat. Neurosci. 4:781 (2001)). Microtubule formation was assayed in the presence of purified GST or GST-cypin, and it was found that cypin promoted microtubule assembly while GST did not (Akum et al., Nature Neurosci. 7:145 (2004)). Furthermore, microtubule assembly was not replicated by merely using amino acids 350-end of cypin (Id.), the tubulin binding region, suggesting that cypin's binding to tubulin heterodimers is not sufficient for the promotion of microtubule assembly.

Example 7

Treatments that increase dendrite number increase cypin

As it has been established cypin plays a physiological role in the regulation of dendrite number, it was expected that cypin protein expression will increase when neurons are treated with agents that have been reported to increase dendrite number, such as KCl or NGF. (Vaillant et al., Neuron 34:985 (2002); McAllister et al., Neuron 17:1057 (1996); Huang et al., Annu. Rev. Neurosci. 24:677 (2001); Zhang, et al., Nat. Neurosci. 4 (Suppl):1207 (2001); Yu & Malenka, Nat. Neurosci. 6:1169 (2003)). To confirm this occurs, cultured rat hippocampal neurons (7 d.i.v.) were treated with increasing amounts of these agents for 3 days. Cypin was assayed for in extracts of these treated neurons by Western blotting. Treatment with increasing amounts of KCl results in increased cypin protein expression (Akum et al., Nature Neurosci. 7:145 (2004)). This increase in cypin protein was accompanied by an increase in guanine deaminase activity (Id.). Furthermore, no increase in actin was observed, showing that the treatments do not upregulate all proteins in the neuron (Id.). Additionally, an increase in cypin expression was observed when neurons were exposed to NGF; however, the increase was not as great as that found with KCl treatment (Id.).

Example 8

Regulators of dendrite number increase cypin protein expression

Cypin regulates dendrite number and treatment of neurons with neurotrophins increases cypin protein levels. BDNF is a neurotrophin known to play an important role in learning and memory. Much of the literature reports that BDNF is the major neurotrophin that increases dendrite number in cortical neurons and that BDNF acts on electrically active neurons (e.g., McAllister et al., Neuron 15:791 (1995); McAllister et al., Neuron 17:1057 (1996); McAllister et al., Neuron 18:767 (1997); Baker et al., Eur. J. Neurosci. 10:1037 (1998); Horch et al., Neuron 23: 353(1999); Lom and Cohen-Cory, J. Neurosci. 19:9928 (1999); Vaillant et al., Neuron 34:985 (2002)). In addition, there are a number of reports supporting the fact that BDNF increases dendrite number (e.g., Tolwani et al., Neuroscience 114:795 (2002). Furthermore, there is evidence that some subpopulations of Alzheimer's patients have altered BDNF or BDNF precursor (pro form) levels (Narisawa-Saito and Nawa, J. Neurochem. 67:1124 (1996); Lapchak et al., Neuroscience 53:297 (1993)).

To assess whether treatment of hippocampal cultures with BDNF increases cypin protein expression, cultures were treated with BDNF and assayed for cypin protein levels by Western blotting. Cypin protein levels were determined to increase with treatments of increasing concentrations of BDNF.

Since BDNF, KCl, and NGF increase cypin protein levels and cypin increases dendrite number in a dose dependent manner, cypin may be a common mediator for extrinsic factors that increase dendrite number. This suggests that cypin is a therapeutic target for cognitive disorders such as Alzheimer's Disease.

Example 9

Neurons enriched in cypin are enriched in nNOS

Neuronal nitric oxide synthase ("nNOS") is an enzyme that is enriched in certain subpopulations of neurons. Inhibitory interneurons are enriched in nNOS and have more dendrites than pyramidal neurons. Furthermore, these neurons are enriched in cypin in the adult rat brain, as compared to pyramidal neurons (Firestein et al., Neuron 24:659 (1999)). Since cypin regulates neuronal morphology and is developmentally regulated in interneurons, it was tested whether cypin is developmentally regulated in these neurons. Results demonstrated that 80% of all neurons that are enriched in cypin at 1 d.i.v., 4, and 7 are also enriched in nNOS and that the majority of neurons enriched in nNOS are also enriched in cypin (Akum et al., Nature Neurosci. 7:145 (2004)). Furthermore, these neurons represented less than 10% of the total neurons, consistent with the number of inhibitory interneurons in culture (Firestein et al., Neuron 24:659 (1999)). This suggests that cypin is enriched in inhibitory neurons very early in culture.

Example 10

Cypin regulates dendrite branching in mature neurons

The main functions of cypin protein are its guanine deaminase activity (mediated by a zinc-binding and a CRMP homology domain) (Akum et al., *Nature Neurosci.* 7:145 (2004), and its PDZ binding domain, which can interact with PSD-95 (Firestein et al., *Neuron* 24:669 (1999)). To determine whether the increase in dendrite number mediated by cypin is due to either of these functions, rat hippocampal neurons were transfected with cDNAs encoding rat cypinΔ (76-84)-GFP (lacking the zinc-binding domain) or rat cypinΔ(350-403)-GFP (lacking CRMP homology domain), as described above. Mutations in the zinc-binding and CRMP domains impaired cypin's ability to increase dendrite number at both 12 and 17 d.i.v. This suggests that cypin guanine deaminase activity is required to induce new dendrites, whereas its interaction with a PDZ protein through its PDZ-binding domain (loss of which, as described above, results in excessive pruning of secondary dendrites in cultres from 12 d.i.v. to 17 d.i.v.) is required to maintain the dendrites as neurons mature.

Example 11

A role for PSD-95 in dendrite branching

The PDZ-binding domain of cypin is known to interact with PSD-95 and plays a role in stabilizing dendrites. To determine whether PSD-95 plays a role in dendrite branching, PSD-95 was overexpressed and dendrites counted at 12 and 17 d.i.v. Overexpression of PSD-95 for forty eight hours (12 d.i.v.) resulted in a decrease in the number of secondary dendrites. By 17 d.i.v., PSD-95 overexpression had no effect on the numbers of primary or secondary dendrites, even though PSD-95 levels persisted until 17 d.i.v. This indicates that the dendrites induced by overexpression of PSD-95 are not stable.

Simultaneous manipulations of cypin and PSD-95 levels were performed to determine whether the effect of one molecule or the other would predominate. Both rat cypin and PSD-95 were overexpressed and dendrites counted at 12 and 17 d.i.v. Overexpressing PSD-95 attenuated the increase in secondary dendrite number promoted by overexpressing cypin at both 12 and 17 d.i.v. The data indicates that elevated PSD-95 levels can suppress dendrite branching, even when cypin levels are elevated, suggesting that cypin might regulate branching by antagonizing PSD-95.

If cypin does regulate dendrite branching by antagonizing PSD-95, then it would be expected that the effects of reducing cypin and overexpressing PSD-95 should affect the same process and thus not be additive. Simultaneously knocking down cypin levels with a 5' end mutated U1 snRNA, as described in Akum et al., *Nature Neurosci.* 7:145 (2004), and overexpressing PSD-95 did not reduce dendrite number at 12 and 17 d.i.v. over that seen with either single manipulation alone. At 12 d.i.v., but not at 17 d.i.v., however, overexpression of PSD-95 while cypin was knocked down brought the number of primary and secondary dendrites back to control levels. This suggests that elevating the levels of PSD-95 occludes the effect of reducing cypin levels, and is consistent with a model whereby cypin regulates dendrite branching, at least in part, by antagonizing PSD-95.

Example 12

Cypin and PSD-95 interactions control dendrite growth rate

Overexpression of cypin can increase dendrite number at both 12 and 17 d.i.v. In contrast, overexpression of cypin lacking the PDZ binding site can induce dendrites at 12 d.i.v. which cannot be detected by 17 d.i.v., suggesting that the dendrites induced by this mutant protein are transient. To examine the pattern of these transient dendrites more closely, the relationship of secondary dendrites to primary dendrites was used as a measure of how "aggressive" the dendrite growth pattern is for each mutant using the slope of secondary versus primary as an indicator of growth rate. Rat cypin-GFP induced more aggressive growth at 12 d.i.v. than at 17 d.i.v. Mutations that impair guanine deaminase activity (cypin(Δ76-84)-GFP and cypin(Δ350-403)-GFP) impaired the aggressive growth induced at 12 d.i.v. by cypin back to the level of GFP. Interestingly, deletion of the PDZ-binding domain (cypin-PDZ-GFP) also reduced the aggressive growth induced at 12 d.i.v. by cypin with a rate equal to that of GFP alone. This indicates that cypin can regulate not only the number of dendrite branches but also the pattern of dendrite branching, and that this regulation is dependent on guanine deaminase activity and PDZ binding.

To investigate how the interaction between cypin and PSD-95 acts to regulate dendrite patterning, the same analysis was applied when PSD-95 was overexpressed. On 12 d.i.v., PSD-95 did not change the basal (GFP) growth rate; however, it did bring the aggressive growth rate of cypin alone back to the basal growth rate. These results support the conclusion that PSD-95 acts to stop secondary branching. Taken together, the data suggest that the interaction between cypin and PSD-95 determines where a dendrite will branch and increases the rate of secondary dendrite growth. If cypin cannot bind to PSD-95 to decrease clustering, as in the case of cypin-PDZ or overexpression of PSD-95, stable secondary dendrites will not form.

Example 13

Knocking down PSD-95 results in increased secondary dendrites

If PSD-95 acts as a stop signal for branching and therefore, decreasing PSD-95 expression should result in an increase in secondary dendrites. To test this hypothesis, a 5' end mutated U1 snRNA corresponding to a region in the 3' UTR of PSD-95 was constructed using the methodology described in Akum et al., *Nature Neurosci.* 7:145 (2004). Neurons were transfected with a cDNA encoding this U1 snRNA and assessed for endogenous PSD-95 levels by immunostaining. When the construct was expressed from 10-12 d.i.v., PSD-95 levels did not change as determined by clusters per area, cluster size, or intensity; however, when the construct was expressed from 10-17 d.i.v., both cluster size and intensity significantly decreased. Dendrite numbers in these neurons, as well as in neurons transfected with vector alone, were then assessed. Knocking down PSD-95 had no significant effect on primary dendrite number. This knockdown, however, significantly increased secondary dendrite number. Furthermore, expression of PSD-95 when endogenous PSD-95 is knocked down brought the number of secondary dendrites back to control levels. This data supports the conclusion that PSD-95 acts as a stop signal for proximal dendrite branching in neurons.

Example 14

Cypin regulates PSD-95 clustering

Cypin decreases PSD-95 and SAP-102 clustering at postsynaptic sites (Firestein et al., *Neuron* 24:659 (1999)). Since binding of cypin to PSD-95 family members plays a role in regulating dendrite number, mutants of cypin were analyzed to determine if they have an effect on the clustering of the PSD-95 at 12 d.i.v. Overexpression of rat cypin resulted in a decreased number and size of endogenous PSD-95 clusters. Furthermore, deletion of the zinc-binding (cypin(Δ76-84)-GFP) or the CRMP-homology (amino cypin (Δ350-403)-GFP) domains of cypin, both of which attenuate cypin's activity to promote increases in dendrite number, result in disruption of cypin's effect on the number of PSD-95 clusters per unit area, but do act like wildtype cypin to decrease cluster size. Deletion of these regions results in guanine deaminase activity with slower kinetics than that of wild-type cypin (Akum et al., Nature Neurosci. 7:145 (2004)). Thus, the slower activity results in a partial phenotype, supporting the conclusion that guanine deaminase activity plays a role in PSD-95 localization by cypin. In addition, cypin lacking the PDZ binding motif (cypin-PDZ-GFP) had no effect on PSD-95 clustering. These results suggest that there are common domains that mediate both cypin's ability to decrease PSD-95 clustering and to increase dendrite number and that these two processes may be related and dependent on guanine deaminase activity. Taken together, the results indicate that the same domains of cypin that are required for dendrite branching are also required to antagonize PSD-95 clustering.

To test the hypothesis that cypin plays a role in regulating the amount of PSD-95 family member proteins that localize to synaptic sites, cypin protein levels in rat hippocampal neurons were knocked down with cDNAs encoding 5'-end mutated U1 snRNAs as described in Akum et al., Nature Neurosci. 7:145 (2004). Although the number of PSD-95 clusters was unchanged, the size and intensity of PSD-95 clusters increased when cypin levels were knocked down by the U1-3'UTR vector. When endogenous cypin was replaced with cypin GFP (U1-3'UTR+cypin-GFP), clusters per unit area returned to control levels, indicating a role for cypin in regulating PSD-95 family member localization.

Example 15 mRNA binding to cypin

Using the methodology of Trifillis et al., RNA 5:1071 (1999); Rodgers et al., Methods 26:115 (2002), and Jiao et al., Biol. Reprod. 66:475(2002), it was found that cypin binds to several mRNAs known be mis-regulated in certain cognitive disorders, such as Cri-du-Chat syndrome, Down Syndrome, and Parkinson's Disease. These mRNAs include the Down Syndrome critical region transcript (Acc. No. U17628), tyrosine-3-monooxygenase (Acc. No. NM_145690)., D-dopachrome tautomerase (Acc. No. NM_001355), and Homo sapien clone HEA6 Cri-du-Chat region mRNA (Acc. No. AF009284). This lends support to the conclusion that cypin is both a marker for cognitive disorders, as well as a target for treatment of such disorders.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for identifying an agonist of cypin polypeptide comprising:
    (a) providing a first and a second sample comprising a cypin polypeptide or fragment thereof having an activity necessary for or associated with promoting a microtubule assembly, wherein said fragment comprises at least one of a collapsin response mediator protein (CRMP) homology domain, a zinc-binding aminohydrolase domain, or a guanine-binding domain;
    (b) contacting said first sample with a candidate agent to be tested for said cypin agonistic activity; and
    (c) measuring the activity of said cypin polypeptide or fragment thereof in said first sample and in said second sample;
    whereby a cypin agonist is identified by measurement of an increase in activity in said first sample as compared to the activity measured in said second sample.

2. The method of claim 1, further comprising contacting a cell capable of dendrite formation and/or branching with the identified agonist and determining whether said agonist increases dendrite formation and/or branching as compared to dendrite formation and/or branching in the absence of such agonist.

3. The method of claim 1, wherein the fragment of cypin polypeptide comprises amino acids 350 to 403 of SEQ ID NO: 1.

4. The method of claim 1, wherein the activity of the cypin polypeptide or the fragment thereof is selected from the group consisting of dendrite formation, dendrite branching, guanine binding, microtubule formation, and tubulin binding.

5. The method of claim 4, wherein the activity of the cypin polypeptide or the fragment thereof is tubulin binding.

6. The method of claim 4, wherein the fragment of the cypin polypeptide comprises amino acid sequence from 350 to 403 of SEQ ID NO: 1.

7. The method of claim 4, wherein the activity of the cypin polypeptide or the fragment thereof is dendrite formation.

8. The method of claim 4, wherein the activity of the cypin polypeptide or the fragment thereof is dendrite branching.

9. The method of claim 4, wherein the activity of the cypin polypeptide or the fragment thereof is guanine binding.

10. The method of claim 4, wherein the activity of the cypin polypeptide or the fragment thereof is microtubule formation.

11. The method of claim 5, wherein the fragment of the cypin polypeptide comprises amino acid sequence from 350 to 403 of SEQ ID NO: 1.

* * * * *

UNITED STATES PATENT AND TRADEMARK OFFICE
CERTIFICATE OF CORRECTION

PATENT NO. : 7,338,769 B2 Page 1 of 1
APPLICATION NO. : 11/033909
DATED : March 4, 2008
INVENTOR(S) : Bonnie Firestein-Miller It is certified that error appears in the above-identified patent and that said Letters Patent is hereby corrected as shown below:

Title page,
Item (75) Inventor, replace "Bonnie Firestein-Miller" with
-- Bonnie L. Firestein-Miller --

Signed and Sealed this

Twenty-eighth Day of October, 2008

JON W. DUDAS
*Director of the United States Patent and Trademark Office*

SEQUENCE LISTING

<160> NUMBER OF SEQ ID NOS: 8

<210> SEQ ID NO 1
<211> LENGTH: 454
<212> TYPE: PRT
<213> ORGANISM: Homo sapiens

<400> SEQUENCE: 1

```
Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Phe Met Pro Gly Leu Val Asp
65                  70                  75                  80

Thr His Ile His Ala Ser Gln Tyr Ser Phe Ala Gly Ser Ser Ile Asp
                85                  90                  95

Leu Pro Leu Leu Glu Trp Leu Thr Lys Tyr Thr Phe Pro Ala Glu His
                100                 105                 110

Arg Phe Gln Asn Ile Asp Phe Ala Glu Glu Val Tyr Thr Arg Val Val
            115                 120                 125

Arg Arg Thr Leu Lys Asn Gly Thr Thr Thr Ala Cys Tyr Phe Ala Thr
```

```
                130                 135                 140
Ile His Thr Asp Ser Ser Leu Leu Ala Asp Ile Thr Asp Lys Phe
145                 150                 155                 160

Gly Gln Arg Ala Phe Val Gly Lys Val Cys Met Asp Leu Asn Asp Thr
                165                 170                 175

Phe Pro Glu Tyr Lys Glu Thr Thr Glu Glu Ser Ile Lys Glu Thr Glu
                180                 185                 190

Arg Phe Val Ser Glu Met Leu Gln Lys Asn Tyr Ser Arg Val Lys Pro
                195                 200                 205

Ile Val Thr Pro Arg Phe Ser Leu Ser Cys Ser Glu Thr Leu Met Gly
210                 215                 220

Glu Leu Gly Asn Ile Ala Lys Thr Arg Asp Leu His Ile Gln Ser His
225                 230                 235                 240

Ile Ser Glu Asn Arg Asp Glu Val Glu Ala Val Lys Asn Leu Tyr Pro
                245                 250                 255

Ser Tyr Lys Asn Tyr Thr Ser Val Tyr Asp Lys Asn Asn Leu Leu Thr
                260                 265                 270

Asn Lys Thr Val Met Ala His Gly Cys Tyr Leu Ser Ala Glu Glu Leu
                275                 280                 285

Asn Val Phe His Glu Arg Gly Ala Ser Ile Ala His Cys Pro Asn Ser
                290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Ile
                340                 345                 350

Leu Leu Ile Asn Lys Val Asn Glu Lys Ser Leu Thr Leu Lys Glu Val
                355                 360                 365

Phe Arg Leu Ala Thr Leu Gly Gly Ser Gln Ala Leu Gly Leu Asp Gly
                370                 375                 380

Glu Ile Gly Asn Phe Glu Val Gly Lys Glu Phe Asp Ala Ile Leu Ile
385                 390                 395                 400

Asn Pro Lys Ala Ser Asp Ser Pro Ile Asp Leu Phe Tyr Gly Asp Phe
                405                 410                 415

Phe Gly Asp Ile Ser Glu Ala Val Ile Gln Lys Phe Leu Tyr Leu Gly
                420                 425                 430

Asp Asp Arg Asn Ile Glu Glu Val Tyr Val Gly Gly Lys Gln Val Val
                435                 440                 445

Pro Phe Ser Ser Ser Val
    450
```

<210> SEQ ID NO 2
<211> LENGTH: 5451
<212> TYPE: DNA
<213> ORGANISM: Homo sapiens
<220> FEATURE:
<221> NAME/KEY: CDS
<222> LOCATION: (184)..(1548)

<400> SEQUENCE: 2

```
gtagggagcc agcccctggg cgcggcctgc agggtaccgg caaccgcccg ggtaagcggg      60
ggcaggacaa ggccggagcc tgtgtccgcc cggcagccgc ccgcagctgc agagagtccc     120
gctgcgtctc cgccgcgtgc gccctcctcg accagcagac ccgcgctgcg ctccgccgct     180
```

```
gac atg tgt gcc gct cag atg ccg ccc ctg gcg cac atc ttc cga ggg      228
Met Cys Ala Ala Gln Met Pro Pro Leu Ala His Ile Phe Arg Gly
 1               5                  10                  15 acg ttc gtc cac tcc acc tgg acc tgc ccc atg gag gtg ctg cgg gat      276
Thr Phe Val His Ser Thr Trp Thr Cys Pro Met Glu Val Leu Arg Asp
                     20                  25                  30 cac ctc ctc ggc gtg agc gac agc ggc aaa ata gtg ttt tta gaa gaa      324
His Leu Leu Gly Val Ser Asp Ser Gly Lys Ile Val Phe Leu Glu Glu
             35                  40                  45 gca tct caa cag gaa aaa ctg gcc aaa gaa tgg tgc ttc aag ccg tgt      372
Ala Ser Gln Gln Glu Lys Leu Ala Lys Glu Trp Cys Phe Lys Pro Cys
         50                  55                  60 gaa ata aga gaa ctg agc cac cat gag ttc ttc atg cct ggg ctg gtt      420
Glu Ile Arg Glu Leu Ser His His Glu Phe Phe Met Pro Gly Leu Val
 65                  70                  75 gat aca cac atc cat gcc tct cag tat tcc ttt gct gga agt agc ata      468
Asp Thr His Ile His Ala Ser Gln Tyr Ser Phe Ala Gly Ser Ser Ile
 80                  85                  90                  95 gac ctg cca ctc ttg gag tgg ctg acc aag tac aca ttt cct gca gaa      516
Asp Leu Pro Leu Leu Glu Trp Leu Thr Lys Tyr Thr Phe Pro Ala Glu
                 100                 105                 110 cac aga ttc cag aac atc gac ttt gca gaa gaa gta tat acc aga gtt      564
His Arg Phe Gln Asn Ile Asp Phe Ala Glu Glu Val Tyr Thr Arg Val
             115                 120                 125 gtc agg aga aca cta aag aat gga aca acc aca gct tgt tac ttt gca      612
Val Arg Arg Thr Leu Lys Asn Gly Thr Thr Thr Ala Cys Tyr Phe Ala
         130                 135                 140 aca att cac act gac tca tct ctg ctc ctt gcc gac att aca gat aaa      660
Thr Ile His Thr Asp Ser Ser Leu Leu Leu Ala Asp Ile Thr Asp Lys
     145                 150                 155 ttt gga cag cgg gca ttt gtg ggc aaa gtt tgc atg gat ttg aat gac      708
Phe Gly Gln Arg Ala Phe Val Gly Lys Val Cys Met Asp Leu Asn Asp
160                 165                 170                 175 act ttt cca gaa tac aag gag acc act gag gaa tcg atc aag gaa act      756
Thr Phe Pro Glu Tyr Lys Glu Thr Thr Glu Glu Ser Ile Lys Glu Thr
                 180                 185                 190 gag aga ttt gtg tca gaa atg ctc caa aag aac tat tct aga gtg aag      804
Glu Arg Phe Val Ser Glu Met Leu Gln Lys Asn Tyr Ser Arg Val Lys
             195                 200                 205 ccc ata gtg aca cca cgt ttt tcc ctc tcc tgc tct gag act ttg atg      852
Pro Ile Val Thr Pro Arg Phe Ser Leu Ser Cys Ser Glu Thr Leu Met
         210                 215                 220 ggt gaa ctg ggc aac att gct aaa acc cgt gat ttg cac att cag agc      900
Gly Glu Leu Gly Asn Ile Ala Lys Thr Arg Asp Leu His Ile Gln Ser
225                 230                 235 cat ata agt gaa aat cgt gat gaa gtt gaa gct gtg aaa aac tta tac      948
His Ile Ser Glu Asn Arg Asp Glu Val Glu Ala Val Lys Asn Leu Tyr
240                 245                 250                 255 ccc agt tat aaa aac tac aca tct gtg tat gat aaa aac aat ctt ttg      996
Pro Ser Tyr Lys Asn Tyr Thr Ser Val Tyr Asp Lys Asn Asn Leu Leu
                 260                 265                 270 aca aat aag aca gtg atg gca cac ggc tgc tac ctc tct gca gaa gaa     1044
Thr Asn Lys Thr Val Met Ala His Gly Cys Tyr Leu Ser Ala Glu Glu
             275                 280                 285 ctg aac gta ttc cat gaa cga gga gca tcc atc gca cac tgt ccc aat     1092
Leu Asn Val Phe His Glu Arg Gly Ala Ser Ile Ala His Cys Pro Asn
         290                 295                 300 tct aat tta tcg ctc agc agt gga ttt cta aat gtg cta gaa gtc ctg     1140
Ser Asn Leu Ser Leu Ser Ser Gly Phe Leu Asn Val Leu Glu Val Leu
305                 310                 315
```

-continued

```
aaa cat gaa gtc aag ata ggg ctg ggt aca gac gtg gct ggt ggc tat     1188
Lys His Glu Val Lys Ile Gly Leu Gly Thr Asp Val Ala Gly Gly Tyr
320                 325                 330                 335 tca tat tcc atg ctt gat gca atc aga aga gca gtg atg gtt tcc aat     1236
Ser Tyr Ser Met Leu Asp Ala Ile Arg Arg Ala Val Met Val Ser Asn
                340                 345                 350 atc ctt tta att aat aag gta aat gag aaa agc ctc acc ctc aaa gaa     1284
Ile Leu Leu Ile Asn Lys Val Asn Glu Lys Ser Leu Thr Leu Lys Glu
            355                 360                 365 gtc ttc aga cta gct act ctt gga gga agc caa gcc ctg ggg ctg gat     1332
Val Phe Arg Leu Ala Thr Leu Gly Gly Ser Gln Ala Leu Gly Leu Asp
        370                 375                 380 ggt gag att gga aac ttt gaa gtg ggc aag gaa ttt gat gcc atc ctg     1380
Gly Glu Ile Gly Asn Phe Glu Val Gly Lys Glu Phe Asp Ala Ile Leu
385                 390                 395 atc aac ccc aaa gca tcc gac tct ccc att gac ctg ttt tat ggg gac     1428
Ile Asn Pro Lys Ala Ser Asp Ser Pro Ile Asp Leu Phe Tyr Gly Asp
400                 405                 410                 415 ttt ttt ggt gat att tct gag gct gtt atc cag aag ttc ctc tat cta     1476
Phe Phe Gly Asp Ile Ser Glu Ala Val Ile Gln Lys Phe Leu Tyr Leu
                420                 425                 430 gga gat gat cga aat att gaa gag gtt tat gtg ggc gga aag cag gtg     1524
Gly Asp Asp Arg Asn Ile Glu Glu Val Tyr Val Gly Gly Lys Gln Val
            435                 440                 445 gtt ccg ttt tcc agc tca gtg taa gaccctcggg cgtctacaaa gttctcctgg   1578
Val Pro Phe Ser Ser Ser Val
        450 gattagcgtg ttctgcatc tcccttgtgc ccaggtggag ttagaaagtc aaaaaatagt   1638 accttgttct tgggatgact atcccttttct gtgtctagtt acagtattca cttgacaaat  1698 agttcgaagg aagttgcact aattctcaac tctggttgag agggttcata aatttcatga   1758 aaatatctcc ctttggagct gctcagactt actttaagct caaacagaag ggaatgctat   1818 tactggtggt gttcctacgg taagacttaa gcaaagcctt tttcatattt gaaaatgtgg   1878 aaagaaaaga tgttcctaaa aggttagata ttttgagcta ataattgcaa aaattagaag   1938 actgaaaatg gacccatgag agtatatttt tatgagggag caaaagttag actgagaaca   1998 aacgttagaa atcacttca gattgtgttt gaaaattata tactgagcat actaatttaa    2058 aaagagaact tgttgaaatt taaaacgtgt ttctaggttg accttgtgtt ttagaaattt   2118 gcacttaatg gaatttgcat ttcagagatg tgttagtgtt gtgctttgcc ttctttggcg   2178 atgaatgtca gaaattgaat gccacatgct ttcataatat agttttgtgc ttcaaagtgt   2238 ttgacagaag ttgggtatta agatttaaa gtctcttagg aatattattc atgtaactcc    2298 atggcataaa tagttgtatt tttgtgtact ttaaaatcaa cttataactg tgagatgtta   2358 ttgcttccat tttattagaa gagaaacaaa ttccatgctt tatggaattt atgtagactg   2418 gagtcttcgt gaactggggc aaatgctggc atccaggagc cgccaatact aacaggacag   2478 gttccattgc catggcctat tccacccaaa caatatgttg tagtttctgg aaattccata   2538 ctcagatatc agtctgctag aactttaaaa tgaaggacaa atcctgttaa agaaatattg   2598 ttaaaaatct ttaaaccctg tgtattgaaa gcactctatt ttctaatttt atccagtttt   2658 ctgtttaact ccttataatg tttaggatat taaaatttta ggataatgaa gagtacataa   2718 tgtcctactt aatatttatg ttaataggac ttaattctta ctagacatct aggaacatta   2778 caaagcaaag actattttta tgcttccata acctagaatt aaaaccaaat tatgacctta   2838
```

```
tgataaatct ttaagtattg gtgtgaatgt tatttaaatt ctatattttt cttatttaat       2898
tacaaatact ataaatgagc aaggaaaagg aatagacttt cttaatatat tataacactc       2958
attcctagag cttaggggtg actctttaat attaccttat agtagaaact ttatgtaata       3018
tagctaactc cgtatttaca gaacaaaaaa acacagttcc ccctcctgta gtataaattt       3078 tatttcaca tacttagcta atttagcagt aattggccca gttttttccc taatagaaat       3138
acttttagat ttgattatgt atacatgaca cctaaagagg gaacaaaagt tagttttatt       3198
tttttaataa acaacagagt tgttttgtg agataagtat cttagtaaac ccaatttcca       3258
gtcttagtct gtatttccaa tatttctaat tcctgagcca cgtcaagat gccttgccaa       3318 atttctcccc atttctctac ggggctagca aaatcttca gctttatccc tcaacccctg       3378
ccaaaggaac ttgattacat ggtgtctaac caaatgagca ggcttaggaa tttagatgag       3438
atgtgtaaga ttcacttaca ggcagtagct gcttctagca tttgcaagat cctacacttt       3498
taccttcttt aagggtgtac attttgatgt tgaacatcag ttttcatgta gacttaggac       3558
tcatgtgcag taaatataaa taagtgtagc atcagaagca gtaggaatgg ccgtatacaa       3618
ccatcctgtt aaacatttaa atttagctct gatagtgtgt taagacctga atatctttcc       3678
tagtaaaaat aggatgtgtt gaaatattta tatgtacttt gatctctcca catcacttat       3738
aacttatgtg ttttatttct ccaagtgcgg tgttcctgaa tgttatgtat gcttttttt       3798 ctgtaccaca ggcattatct atacctgggg ccagattttc tgcactttga aatgttgcct       3858
ttgcctaatg taggttgact ttctgaattg tggagaggca cttttccaag ccaatcttat       3918
ttgtcacttt ttgtttttaat atcttgctct ctgacaggaa agaaacaatt cacttaccag       3978
cctcctcacc ccatcctcca ccatttcctt aatgttccat ggtattttca acggaataca       4038
ctttgaaagg taaaaacaat tcaaaagtat cgattatcat aaattcacaa atatttttg       4098 caaccagaac acaaaagcag gctagtcagc taaggtaaat ttcattttca acgagaggg        4158 aaacatggga agtaaaagat taggatgtga aaggttgtcc taaacagacc aaggagactg       4218
ttccctaatt tattctcttg gctggttctc tcattgaatt atcagacccc aagaggagat       4278
attggaacag gctcccttca tgccaagggt ctttctaagt taatactgtg agcattgagc       4338
ccccattaaa actcttttt acttcagaaa gaattttaca ggttaaaggg aaagaaatgg        4398
tgggaaactc tccccgtaat gcttagccaa ctttaaagtg tacccttcaa tatccccatt       4458
ggcaactgca gctgagatct tagagaggaa atataaccgg tgtgagatct agcaatgcat       4518
tttgaatctt cactccctac caggctcttc ctatttttaa tctcttcacc tcagaactag       4578
acatatggag agctttaaag gcaagctgga aggcacattg tatcaattct accttgtgct       4638
atacgtagga gagatccaaa atttggatgc ttctggagac tcttagacat cttttcattg       4698
ttgtccattt ttaaagttga tgattgctgg aaacattcac acgcttaaaa gcaatggtgt       4758
gagttattaa tgggtaaact aagaagtgtt ataggcaatg acttgaaatg gttttttaaat       4818 tgtatggatt gttaagaatt gttgaaaaaa aattttttt ttttggacag cttcaaggag        4878
atgttagcaa tttcagatat actagccagt ttaggtatga ctttggaagt gcagaaacag       4938
aaggatactg ttagaaaatc ctaacattgg tctccgtgca tgtgttcaca cctggtctca       4998 ctgccttttcc ttcccacaga cctgagtgtg aaagactgag agttgaggag ttactttgtg      5058
gatcttgtcc aaatttagtg aaatgtggaa gtcaaccaga ccaatgatgg aattaaatgt       5118
aaattccaag agggctttca cagtccacag ggttcaaatg acttgggtaa cagaagttat       5178
tcttagctta cctgttatgt gacagtgatt tacctgtcca tttccaaccc aaaagcctgt       5238
```

-continued

```
cagaaagcat tctttagaga aaaccacttt acatttgttg ttaaactcct gatcgctact    5298
cttaagaata tacatgtatg tattcatagg aacatttttt ctcaatattt gtatgattcg    5358
cttactgtta ttgtgctgag tgagctcctg tgtgcttcag acaaaaataa atgagacttt    5418
gtgtttacgt taaaaaaaaa aaaaaaaaa aaa                                  5451
```

<210> SEQ ID NO 3
<211> LENGTH: 454
<212> TYPE: PRT
<213> ORGANISM: Pongo pygmaeus

<400> SEQUENCE: 3

```
Met Cys Ala Ala Gln Met Pro Pro Leu Ala His Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ala
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Phe Met Pro Gly Leu Val Asp
65                  70                  75                  80

Thr His Ile His Ala Ser Gln Tyr Ser Phe Ala Gly Ser Asn Ile Asp
                85                  90                  95

Leu Pro Leu Leu Glu Trp Leu Thr Lys Tyr Thr Phe Pro Ala Glu His
            100                 105                 110

Arg Phe Gln Asn Thr Asp Phe Ala Glu Glu Val Tyr Thr Arg Val Val
        115                 120                 125

Arg Arg Thr Leu Lys Asn Gly Thr Thr Thr Ala Cys Tyr Phe Ala Thr
130                 135                 140

Ile His Thr Asp Ser Ser Leu Leu Leu Ala Asp Ile Thr Asp Lys Phe
145                 150                 155                 160

Gly Gln Arg Ala Phe Val Gly Lys Val Cys Met Asn Leu Asn Asp Thr
                165                 170                 175

Phe Pro Glu Tyr Asn Glu Thr Thr Glu Glu Ser Ile Lys Glu Thr Glu
            180                 185                 190

Arg Phe Val Ser Glu Met Leu Gln Arg Lys Tyr Ser Arg Val Lys Pro
        195                 200                 205

Ile Val Thr Pro Arg Phe Ser Leu Ser Cys Ser Glu Thr Leu Met Gly
    210                 215                 220

Asp Leu Gly Asn Ile Ala Lys Thr His Asp Leu His Ile Gln Ser His
225                 230                 235                 240

Ile Ser Glu Asn Arg Asp Glu Val Glu Ala Val Lys Asn Leu Tyr Pro
                245                 250                 255

Ser Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Ala Glu Glu Leu
        275                 280                 285

Asn Val Phe His Glu Arg Gly Ala Ser Ile Ala His Cys Pro Asn Ser
    290                 295                 300

Asn Leu Ser Leu Ser Ser Gly Phe Leu Asn Val Leu Glu Val Leu Lys
305                 310                 315                 320

His Glu Val Lys Ile Gly Leu Gly Thr Asp Val Ala Gly Gly Tyr Ser
                325                 330                 335
```

```
Tyr Ser Met Leu Asp Ala Ile Arg Arg Ala Val Met Val Ser Asn Ile
        340                 345                 350
Leu Leu Ile Asn Lys Val Asn Glu Lys Ser Leu Thr Leu Lys Glu Val
        355                 360                 365
Phe Arg Leu Ala Thr Leu Gly Gly Ser Gln Ala Leu Gly Leu Asp Gly
        370                 375                 380
Glu Ile Gly Asn Phe Glu Val Gly Lys Glu Phe Asp Ala Ile Leu Ile
385                 390                 395                 400
Asn Pro Lys Ala Ser Asp Ser Pro Ile Asp Leu Phe Tyr Gly Asp Phe
                405                 410                 415
Phe Gly Asp Ile Ser Glu Ala Val Ile Gln Lys Phe Leu Tyr Leu Gly
                420                 425                 430
Asp Asp Arg Asn Ile Glu Glu Val Tyr Val Gly Gly Lys Gln Val Val
            435                 440                 445
Pro Phe Ser Ser Ser Val
        450

<210> SEQ ID NO 4
<211> LENGTH: 5354
<212> TYPE: DNA
<213> ORGANISM: Pongo pygmaeus
<220> FEATURE:
<221> NAME/KEY: CDS
<222> LOCATION: (122)..(1486)

<400> SEQUENCE: 4
gaggataagg ccggagccgg tgtccgcccg acagccgccc gcagctgcag agagtcccgc    60
tgcgcttccg ccgcgtgcgc cctcctcgac cagcagaccc gcgctgcgct ccgccgctga   120 c atg tgt gcc gct cag atg ccg ccc ctg gcg cac atc ttc cga ggg acg   169
  Met Cys Ala Ala Gln Met Pro Pro Leu Ala His Ile Phe Arg Gly Thr
    1               5                  10                  15 ttc gtc cac tcc acc tgg acc tgc ccc atg gag gtg ctg cgg gat cac    217
Phe Val His Ser Thr Trp Thr Cys Pro Met Glu Val Leu Arg Asp His
                20                  25                  30 ctc ctc ggc gtg agc gac agc ggc aaa ata gtg ttt tta gaa gaa gca    265
Leu Leu Gly Val Ser Asp Ser Gly Lys Ile Val Phe Leu Glu Glu Ala
            35                  40                  45 tct caa caa gaa aaa ctg gcc aaa gaa tgg tgc ttc aag cca tgt gaa    313
Ser Gln Gln Glu Lys Leu Ala Lys Glu Trp Cys Phe Lys Pro Cys Glu
        50                  55                  60 ata aga gaa ctg agc cac cat gag ttc ttc atg cct ggg ctg gtt gat    361
Ile Arg Glu Leu Ser His His Glu Phe Phe Met Pro Gly Leu Val Asp
65                  70                  75                  80 aca cac atc cat gcc tct cag tat tcc ttt gct gga agt aac ata gac    409
Thr His Ile His Ala Ser Gln Tyr Ser Phe Ala Gly Ser Asn Ile Asp
                85                  90                  95 ctg cca ctc ttg gag tgg ctg acc aag tac aca ttt cct gca gaa cac    457
Leu Pro Leu Leu Glu Trp Leu Thr Lys Tyr Thr Phe Pro Ala Glu His
                100                 105                 110 aga ttc cag aac act gac ttt gcg gaa gaa gta tat acc aga gtt gtc    505
Arg Phe Gln Asn Thr Asp Phe Ala Glu Glu Val Tyr Thr Arg Val Val
            115                 120                 125 agg aga aca cta aag aat gga aca acc aca gct tgt tac ttt gca aca    553
Arg Arg Thr Leu Lys Asn Gly Thr Thr Thr Ala Cys Tyr Phe Ala Thr
        130                 135                 140 att cac act gac tca tct ctg ctc ctt gcc gac att aca gat aaa ttt    601
Ile His Thr Asp Ser Ser Leu Leu Leu Ala Asp Ile Thr Asp Lys Phe
145                 150                 155                 160
```

-continued

| | |
|---|---|
| gga cag cgg gca ttt gtg ggc aaa gtt tgc atg aat ttg aat gac act<br>Gly Gln Arg Ala Phe Val Gly Lys Val Cys Met Asn Leu Asn Asp Thr<br>                165                    170                    175 | 649 |
| ttt cca gaa tac aat gag acc act gag gaa tcg atc aag gaa acc gag<br>Phe Pro Glu Tyr Asn Glu Thr Thr Glu Glu Ser Ile Lys Glu Thr Glu<br>         180                    185                    190 | 697 |
| aga ttt gtg tca gaa atg ctc caa agg aaa tat tct aga gtg aag ccc<br>Arg Phe Val Ser Glu Met Leu Gln Arg Lys Tyr Ser Arg Val Lys Pro<br>         195                    200                    205 | 745 |
| ata gtg aca cca cgt ttt tcc ctc tcc tgc tct gag act ttg atg ggt<br>Ile Val Thr Pro Arg Phe Ser Leu Ser Cys Ser Glu Thr Leu Met Gly<br>210                    215                    220 | 793 |
| gat ctc ggc aac att gct aaa acc cat gat ttg cac att cag agc cat<br>Asp Leu Gly Asn Ile Ala Lys Thr His Asp Leu His Ile Gln Ser His<br>225                    230                    235                    240 | 841 |
| ata agt gaa aat cgt gat gaa gtt gaa gct gtg aaa aac tta tac ccc<br>Ile Ser Glu Asn Arg Asp Glu Val Glu Ala Val Lys Asn Leu Tyr Pro<br>                  245                    250                    255 | 889 |
| agt tat aaa aac tac aca gat gtg tat gat aaa aac aat ctt ttg aca<br>Ser Tyr Lys Asn Tyr Thr Asp Val Tyr Asp Lys Asn Asn Leu Leu Thr<br>         260                    265                    270 | 937 |
| aat aag aca gtg atg gca cac ggc tgc tac ctc tct gca gaa gaa ctg<br>Asn Lys Thr Val Met Ala His Gly Cys Tyr Leu Ser Ala Glu Glu Leu<br>         275                    280                    285 | 985 |
| aat gta ttc cat gaa cga gga gca tcc atc gca cac tgt ccc aat tct<br>Asn Val Phe His Glu Arg Gly Ala Ser Ile Ala His Cys Pro Asn Ser<br>290                    295                    300 | 1033 |
| aat tta tcg ctc agc agt gga ttt cta aat gtg cta gaa gtc ctg aaa<br>Asn Leu Ser Leu Ser Ser Gly Phe Leu Asn Val Leu Glu Val Leu Lys<br>305                    310                    315                    320 | 1081 |
| cat gaa gtc aag ata ggg ctg ggt aca gac gtg gct ggt ggc tat tcg<br>His Glu Val Lys Ile Gly Leu Gly Thr Asp Val Ala Gly Gly Tyr Ser<br>                  325                    330                    335 | 1129 |
| tat tcc atg ctt gat gca atc aga aga gca gtg atg gtt tcc aat atc<br>Tyr Ser Met Leu Asp Ala Ile Arg Arg Ala Val Met Val Ser Asn Ile<br>         340                    345                    350 | 1177 |
| ctt tta att aat aag gta aat gag aaa agc ctc acc ctc aaa gaa gtc<br>Leu Leu Ile Asn Lys Val Asn Glu Lys Ser Leu Thr Leu Lys Glu Val<br>                  355                    360                    365 | 1225 |
| ttc aga cta gct act ctt gga gga agc caa gcc ctg ggg ctg gat ggt<br>Phe Arg Leu Ala Thr Leu Gly Gly Ser Gln Ala Leu Gly Leu Asp Gly<br>370                    375                    380 | 1273 |
| gag att gga aac ttt gaa gtg ggc aag gaa ttt gat gcc atc ctg atc<br>Glu Ile Gly Asn Phe Glu Val Gly Lys Glu Phe Asp Ala Ile Leu Ile<br>385                    390                    395                    400 | 1321 |
| aac ccc aaa gca tcc gac tct ccc att gac ctg ttt tat ggg gac ttt<br>Asn Pro Lys Ala Ser Asp Ser Pro Ile Asp Leu Phe Tyr Gly Asp Phe<br>                  405                    410                    415 | 1369 |
| ttt ggt gat att tct gag gct gtt atc cag aaa ttc ctc tat cta gga<br>Phe Gly Asp Ile Ser Glu Ala Val Ile Gln Lys Phe Leu Tyr Leu Gly<br>         420                    425                    430 | 1417 |
| gat gat cga aat att gaa gag gtt tat gtg ggc gga aag cag gtg gtt<br>Asp Asp Arg Asn Ile Glu Glu Val Tyr Val Gly Gly Lys Gln Val Val<br>                  435                    440                    445 | 1465 |
| ccg ttt tcc agc tca gtg taa gaccctcggg cgtctatgaa gttctcctgg<br>Pro Phe Ser Ser Ser Val<br>         450 | 1516 |
| gattagcgtg gttctgcatc tcccttgtgc ccaggtggag ttagaaagtc aaaaaatagt | 1576 |

```
accttgttct tgggatggct atcccttcct gtgtctagtt acagtattca cttgacaaat    1636
agttcgaagg aagttgcgct aattctcaac tctggttgag agggttcata aatttcatga    1696
aaatgtctcc ctttggagct gctcagactt actttaagct caaacagaag ggaatgctat    1756
tactggtggt gttcctacga taagacttaa gcaaagcctt tttcatattt gaaaatatgg    1816
aaagaaaaga tgttcctaaa aggttagata ttttgagcta ataattgcaa aaattagaag    1876
actgaaaatg gacccatgag agtatatttt tatgagggag caaaagttag actgagaaca    1936
aatgttagaa aatcacttca gattgtgttt gaaaattata taccgagcat actaatttaa    1996
aaagagaact tgttgaattt taaaacgtgt ttctaggttg accttgtgtt ttagaaattt    2056
gcacttaatg gaatttgcat ttcagagatg tgttagtgtt gtgctttgcc ttctttgggg    2116
atgaatgtca gaaattgaat gccacatgct ttcataatat agttttgtgc ttcaaagtgt    2176
ttgacagaag ttgggtatta aagatttaaa gtctcttagg aatattattc atgtaactcc    2236
atggtataaa tagttgtatt tttgtgtact ttaaaatcaa cttataactg tgagatgtta    2296
ttgcttccat tttattagaa gagaaacaaa ttccatgctt tatggaaatt atgtagactg    2356
gagtcttcgt gaactggggc aagtgctggc atccaggagc cgccaatact aacaggacag    2416
gttccattgc catggcctat tccatccaaa caatgtgttg tagtttctgg aaattccata    2476
ctcagatatc agtctgctag aactttaaaa tgaaggacaa atcctgttaa agaaatattg    2536
ttaaaaatct ttaaaccctg tgtattgaaa gcactctatt ttctaatttt atccagtttt    2596
ctgtttaacc ccttataatt tttaggtatt tagaatttc ggataatgaa gagtacataa    2656
tgtcctactt aatatttatg ttaataggac ttaattctta ctagacatct aggaacatta    2716
caaagcaaag aatattttta tgcttccata acctagaatt aaaaccaaat tatgacctta    2776
tgataaatct ttaagtattg gtgtgaatgt tatttaaatt ctatattttt cttatttaat    2836
tacaaatact ataattgagc aaggaaaagg aatagacttt cttcatatat tataacactc    2896
attcctagag cttagggtg actctttaat attacccta tagtagaaaa ctttatgtaa    2956
tatagctaac tccatatta cagaacaaaa aacacagttc ccctcctgt agtataaatt    3016
ttatttcac atacttggct aatttagcag taattggccc catttttcc ctaatagaaa    3076
tacttttaga tttgattatg tatacatgac acctaaagag ggaacaaaag tttagttta    3136
tttttttaat aaacaacaga gtttgttttg tgagataagt agcttagtaa acccagtttc    3196
cagtcttagt ctgtatttcc aatatttcta attcctgagc catgtcaaag atgccttgcc    3256
aaatttctcc ccatttctct acggggctag caagaatctt cagctttatc cctcaacccc    3316
tgccaaagga acttgattac atggtgtcta accaaatgag taggcttagg aatttggatg    3376
aaatgtgtaa gattcactta caggcagtag ctgcttctag catttgcaag atcctacact    3436
tttaccttct ttaagggtgt acattttgat gttgaacatc agttttcatg tagacttagg    3496
actcatgtgc agtaaatata aataagtgta gcatcagaag cagtaggaat ggccgtatac    3556
aaccatcctg ttaaacattt aaatttagct ctgatagtgt gttaagacct gaatatcttt    3616
cctagtaaaa ataggatgtg ttgaaatgtt tatatgtact ttgatctctc cgcatcactt    3676
ataacttatg tgctttattt ctccaagtgc ggtgttcctg aatgttgtat atgctttttt    3736
ttttctgtac cacaggcatt agctatacct ggggccagat tttctgcact ttgaaatgta    3796
gcctttgcct aatgtaggtt gactttctaa attgtggaga ggcacttttc caagccaatc    3856
ttatttgtca cttttttgttt taatatcttg ctctctgaca ggaaagaaac aattcactta    3916
ccagcctcct cacccatcc tccaccattt ccttaatgtt ccatggtatt ttcaacagaa    3976
```

-continued

```
tacactttga aaggtaaaaa caattcaaaa gtatcgatta tcataaattc acaaaatatt    4036
tttacaacca gaacacaaaa gcaggctagt cagctaaggt aaatttcatt ttcaaatgag    4096
agggaaacat gggaagtaaa agattaggat gtgaaaggtt gtcctaaaca gaccaaggag    4156
actgtttcct aatttattct cttggctggt tctctcgttg aattatcaga ccccaagagg    4216
aaatcttgga acaggctccc ttcatgccaa gggtctttct aagttaatgc tgtgagcatt    4276
gagcccccat taaaactctt ttttacttca gaaagacttc tacaggttaa agggaaagaa    4336
atggtgggaa actctccccg taatgctag ccaactttaa agtgtaccct ccaatatccc     4396
cattggcaac tgcagctgag atcttagaga ggaaatataa ccggtgtgag gtctagcaat    4456
gcattttgaa tcttcactcc ctaccaggct cttcctattt ttaatctctt cacctcagaa    4516
ctagacatat ggagagcttt aaaggcaagc tggaaggcac attgtatcaa ttctaccttg    4576
tgctgtacgt gggagagatc caaaatttgg atgcttctgg agactgttag acatcttttc    4636
attgttgtcc atttttaaag ttgatgatga ttgctggaaa cattcacatg cttaaaagca    4696
atggtgtgag ttattaacgg gtaaactaag aagtatgtta taggcaatga cttgaaatgg    4756
tttttaaatt gtatggattg ttaagaattt ttgaaatttt ttttttttt tggacagctt      4816 caaggagatg ttagcaattt cagatatact agccagttta ggtatgactt tggaagtgca    4876
gaaacagaag gatactgtta gaaaatccta acattggtct ccatgcatgt gttcacacct    4936
ggtctcactg cctttccttc tcatagcccct gagtgtgaaa gattgagagt tgaggaattg   4996
ctttgtggat cttgtccaaa tttagtgaaa tgtggagtca accaggccaa tgatgaaatt    5056
aaatgtaaat tccaagaggg ctttcacagt ccacagggct caaatgactt gggtaacaga    5116
agttattctt agcttacctg ttatgtgaca gtgatttacc tgtccatttc caacccaaaa    5176
gcctgtcaga aagcattctt tagagaaaac cactttacat ttgttgttaa actcctgatt    5236
gctactctta agaatataca tgtatgtatt cataggaaca ttttttttctc aatatttgta   5296 tgattcgctt actgttattg tgctgagtga gctcctatgt gcttcagaca aaaataaa     5354
```

<210> SEQ ID NO 5
<211> LENGTH: 454
<212> TYPE: PRT
<213> ORGANISM: Rattus norvegicus

<400> SEQUENCE: 5

```
Met Cys Ala Ala Arg Thr Pro Gln Leu Ala Leu Ile Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ser
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Asp Trp Leu Asn Lys Tyr Thr Phe Pro Thr Glu Lys
            100                 105                 110

Arg Phe Gln Ser Thr Asp Val Ala Glu Glu Val Tyr Thr Arg Val Val
        115                 120                 125
```

```
Arg Arg Thr Leu Lys Asn Gly Thr Thr Thr Ala Cys Tyr Phe Gly Thr
            130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asn Thr
                165                 170                 175

Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Ser Arg Val Lys Pro
        195                 200                 205

Ile Val Thr Pro Arg Phe Ser Leu Ser Cys Thr Glu Thr Leu Met Ser
210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Gly Tyr Lys Asn Tyr Thr Asp Val Tyr Asp Lys Asn Asn Leu Leu Thr
            260                 265                 270

Asn Lys Thr Val Met Ala His Gly Cys Tyr Leu Ser Glu Glu Leu
        275                 280                 285

Asn Val Phe Ser Glu Arg Gly Ala Ser Ile Ala His Cys Pro Asn Ser
290                 295                 300

Asn Leu Ser Leu Ser Ser Gly Leu Leu Asn Val Leu Asp Val Leu Lys
305                 310                 315                 320

His Lys Val Lys Ile Gly Leu Gly Thr Asp Val Ala Gly Tyr Ser
                325                 330                 335

Tyr Ser Met Leu Asp Ala Ile Arg Arg Ala Val Met Val Ser Asn Val
                340                 345                 350

Leu Leu Ile Asn Lys Val Asn Glu Lys Ser Leu Thr Leu Lys Glu Val
            355                 360                 365

Phe Arg Leu Ala Thr Leu Gly Gly Ser Gln Ala Leu Gly Leu Asp Arg
370                 375                 380

Glu Ile Gly Asn Phe Glu Val Gly Lys Asp Phe Asp Ala Leu Leu Ile
385                 390                 395                 400

Asn Pro Arg Ala Ser Asp Ser Pro Ile Asp Leu Phe Cys Gly Asp Phe
                405                 410                 415

Val Gly Asp Ile Ser Glu Ala Val Ile Gln Lys Phe Leu Tyr Leu Gly
            420                 425                 430

Asp Asp Arg Asn Ile Glu Glu Val Tyr Val Gly Gly Lys Gln Val Val
        435                 440                 445

Pro Phe Ser Ser Ser Val
    450

<210> SEQ ID NO 6
<211> LENGTH: 1460
<212> TYPE: DNA
<213> ORGANISM: Rattus norvegicus
<220> FEATURE:
<221> NAME/KEY: CDS
<222> LOCATION: (47)..(1411)

<400> SEQUENCE: 6
ggtgcaccct ctttggtcag tgaacttgcg ctgccccgct gctgcc atg tgt gcg      55
                                               Met Cys Ala
                                                 1 gct cgg acg ccg cag ctg gcg ctc atc ttc cga ggg act ttc gtc cac    103
```

| | | | | | | | | | | | | | | |
|---|---|---|---|---|---|---|---|---|---|---|---|---|---|---|
| Ala | Arg | Thr | Pro | Gln | Leu | Ala | Leu | Ile | Phe | Arg | Gly | Thr | Phe | Val | His |
| | 5 | | | | 10 | | | | | 15 | | | | |

```
tcc acc tgg acc tgc ccc atg gag gtg ctt cgc gat cac ctt ctt ggc      151
Ser Thr Trp Thr Cys Pro Met Glu Val Leu Arg Asp His Leu Leu Gly
 20              25                  30                  35 gtg agc gac agc ggc aaa ata gtg ttt cta gaa gaa tca tct cag caa      199
Val Ser Asp Ser Gly Lys Ile Val Phe Leu Glu Glu Ser Ser Gln Gln
                 40                  45                  50 gaa aag ctg gcc aaa gaa tgg tgc ttc aaa ccg tgt gag atc aga gag      247
Glu Lys Leu Ala Lys Glu Trp Cys Phe Lys Pro Cys Glu Ile Arg Glu
             55                  60                  65 ctg agc cac cat gag ttc ttc atg cca ggc ctt gtt gat aca cac atc      295
Leu Ser His His Glu Phe Phe Met Pro Gly Leu Val Asp Thr His Ile
         70                  75                  80 cat gcc cct cag tat gcc ttt gct gga agc aac gtc gac ctg cca ctt      343
His Ala Pro Gln Tyr Ala Phe Ala Gly Ser Asn Val Asp Leu Pro Leu
     85                  90                  95 ttg gat tgg ctg aac aag tat aca ttt cct aca gaa aaa agg ttc cag      391
Leu Asp Trp Leu Asn Lys Tyr Thr Phe Pro Thr Glu Lys Arg Phe Gln
100                 105                 110                 115 agc acc gat gtg gct gaa gaa gtc tac act aga gtc gtt agg aga aca      439
Ser Thr Asp Val Ala Glu Glu Val Tyr Thr Arg Val Val Arg Arg Thr
                120                 125                 130 cta aag aac ggc acc acc acg gca tgc tac ttt gga aca att cac act      487
Leu Lys Asn Gly Thr Thr Thr Ala Cys Tyr Phe Gly Thr Ile His Thr
            135                 140                 145 gac tca tcc ctg atc ctt gcg gaa att aca gat aaa ttt ggg cag cga      535
Asp Ser Ser Leu Ile Leu Ala Glu Ile Thr Asp Lys Phe Gly Gln Arg
        150                 155                 160 gca ttt gtg ggc aaa gta tgc atg gat tta aat aac act gtt cca gaa      583
Ala Phe Val Gly Lys Val Cys Met Asp Leu Asn Asn Thr Val Pro Glu
165                 170                 175 tac aag gag acc acc gag gag tca gtc aag gag aca gag aga ttt gtg      631
Tyr Lys Glu Thr Thr Glu Glu Ser Val Lys Glu Thr Glu Arg Phe Val
180                 185                 190                 195 tca gaa atg ctt caa aag aat tat tca agg gtg aaa ccc ata gtg acc      679
Ser Glu Met Leu Gln Lys Asn Tyr Ser Arg Val Lys Pro Ile Val Thr
                200                 205                 210 ccg cga ttt tct ctt tct tgc acg gag act ctg atg agt gaa ctt ggc      727
Pro Arg Phe Ser Leu Ser Cys Thr Glu Thr Leu Met Ser Glu Leu Gly
            215                 220                 225 aac atc gcc aag act cat gat ctg tac atc cag agc cat ata agt gaa      775
Asn Ile Ala Lys Thr His Asp Leu Tyr Ile Gln Ser His Ile Ser Glu
        230                 235                 240 aat cgt gaa gaa att gaa gct gtg aaa agc tta tac cct ggc tac aaa      823
Asn Arg Glu Glu Ile Glu Ala Val Lys Ser Leu Tyr Pro Gly Tyr Lys
245                 250                 255 aac tac aca gat gtc tat gat aaa aac aat ctt ctg aca aac aaa aca      871
Asn Tyr Thr Asp Val Tyr Asp Lys Asn Asn Leu Leu Thr Asn Lys Thr
260                 265                 270                 275 gtg atg gct cat ggc tgc tac ctt tct gaa gaa gag ctg aac gtc ttc      919
Val Met Ala His Gly Cys Tyr Leu Ser Glu Glu Glu Leu Asn Val Phe
                280                 285                 290 agt gaa cga gga gca tcc att gca cat tgt ccc aac tct aat ctg tcg      967
Ser Glu Arg Gly Ala Ser Ile Ala His Cys Pro Asn Ser Asn Leu Ser
            295                 300                 305 ctg agc agt ggc tta ctg aac gtg ctc gat gtc ctg aag cat aaa gtg     1015
Leu Ser Ser Gly Leu Leu Asn Val Leu Asp Val Leu Lys His Lys Val
        310                 315                 320
```

```
                                             -continued
aag ata ggg ctt ggg aca gat gtg gct ggt ggt tac tcc tat tcc atg      1063
Lys Ile Gly Leu Gly Thr Asp Val Ala Gly Gly Tyr Ser Tyr Ser Met
325                 330                 335 ctt gac gcc atc cga aga gca gtg atg gtt tcc aac gtc ctc tta att      1111
Leu Asp Ala Ile Arg Arg Ala Val Met Val Ser Asn Val Leu Leu Ile
340                 345                 350                 355 aat aag gtg aat gag aaa agc ctc acc ctc aaa gaa gtc ttc aga cta      1159
Asn Lys Val Asn Glu Lys Ser Leu Thr Leu Lys Glu Val Phe Arg Leu
                360                 365                 370 gcc act ctt gga gga agc caa gcc ctg ggg ctt gat cgt gaa att gga      1207
Ala Thr Leu Gly Gly Ser Gln Ala Leu Gly Leu Asp Arg Glu Ile Gly
            375                 380                 385 aac ttt gag gtc ggc aag gat ttt gat gcc ctc ttg atc aac ccc aga      1255
Asn Phe Glu Val Gly Lys Asp Phe Asp Ala Leu Leu Ile Asn Pro Arg
        390                 395                 400 gca tcg gac tct ccc att gat ctg ttt tgt ggg gat ttc gtt ggt gat      1303
Ala Ser Asp Ser Pro Ile Asp Leu Phe Cys Gly Asp Phe Val Gly Asp
    405                 410                 415 att tct gag gct gtt atc cag aag ttc ctc tat cta gga gat gac cga      1351
Ile Ser Glu Ala Val Ile Gln Lys Phe Leu Tyr Leu Gly Asp Asp Arg
420                 425                 430                 435 aac att gag gag gtt tat gtg ggt gga aag cag gtc gtt cca ttc tcc      1399
Asn Ile Glu Glu Val Tyr Val Gly Gly Lys Gln Val Val Pro Phe Ser
                440                 445                 450 agc tcc gtg taa ggcccttgga catccatgac gctctcctgg gaggacatga          1451
Ser Ser Val gtctgctat                                                            1460

<210> SEQ ID NO 7
<211> LENGTH: 454
<212> TYPE: PRT
<213> ORGANISM: Mus musculus

<400> SEQUENCE: 7

Met Cys Ala Ala Arg Thr Pro Pro Leu Ala Leu Val Phe Arg Gly Thr
1               5                   10                  15

Phe Val His Ser Thr Trp Thr Cys Pro Met Glu Val Leu Arg Asp His
                20                  25                  30

Leu Leu Gly Val Ser Asp Ser Gly Lys Ile Val Phe Leu Glu Glu Ser
            35                  40                  45

Ser Gln Gln Glu Lys Leu Ala Lys Glu Trp Cys Phe Lys Pro Cys Glu
        50                  55                  60

Ile Arg Glu Leu Ser His His Glu Phe Phe Met Pro Gly Leu Val Asp
65                  70                  75                  80

Thr His Ile His Ala Pro Gln Tyr Ala Phe Ala Gly Ser Asn Val Asp
                85                  90                  95

Leu Pro Leu Leu Glu Trp Leu Asn Lys Tyr Thr Phe Pro Thr Glu Gln
            100                 105                 110

Arg Phe Arg Ser Thr Asp Val Ala Glu Glu Val Tyr Thr Arg Val Val
        115                 120                 125

Arg Arg Thr Leu Lys Asn Gly Thr Thr Thr Ala Cys Tyr Phe Gly Thr
    130                 135                 140

Ile His Thr Asp Ser Ser Leu Ile Leu Ala Glu Ile Thr Asp Lys Phe
145                 150                 155                 160

Gly Gln Arg Ala Phe Val Gly Lys Val Cys Met Asp Leu Asn Asp Thr
                165                 170                 175
```

-continued

```
Val Pro Glu Tyr Lys Glu Thr Thr Glu Glu Ser Val Lys Glu Thr Glu
            180                 185                 190

Arg Phe Val Ser Glu Met Leu Gln Lys Asn Tyr Pro Arg Val Lys Pro
        195                 200                 205

Ile Val Thr Pro Arg Phe Thr Leu Ser Cys Thr Glu Thr Leu Met Ser
    210                 215                 220

Glu Leu Gly Asn Ile Ala Lys Thr His Asp Leu Tyr Ile Gln Ser His
225                 230                 235                 240

Ile Ser Glu Asn Arg Glu Glu Ile Glu Ala Val Lys Ser Leu Tyr Pro
                245                 250                 255

Ser Tyr Lys Asn Tyr Thr Asp Val Tyr Asp Lys Asn Asn Leu Leu Thr
                260                 265                 270

Asn Lys Thr Val Met Ala His Gly Cys Tyr Leu Ser Glu Glu Leu
            275                 280                 285

Asn Ile Phe Ser Glu Arg Gly Ala Ser Ile Ala His Cys Pro Asn Ser
        290                 295                 300

Asn Leu Ser Leu Ser Ser Gly Leu Leu Asn Val Leu Glu Val Leu Lys
305                 310                 315                 320

His Lys Val Lys Ile Gly Leu Gly Thr Asp Val Ala Gly Gly Tyr Ser
                325                 330                 335

Tyr Ser Met Leu Asp Ala Ile Arg Arg Ala Val Met Val Ser Asn Val
                340                 345                 350

Leu Leu Ile Asn Lys Val Asn Glu Lys Asn Leu Thr Leu Lys Glu Val
            355                 360                 365

Phe Arg Leu Ala Thr Leu Gly Gly Ser Gln Ala Leu Gly Leu Asp Ser
        370                 375                 380

Glu Ile Gly Asn Phe Glu Val Gly Lys Glu Phe Asp Ala Leu Leu Ile
385                 390                 395                 400

Asn Pro Arg Ala Ser Asp Ser Pro Ile Asp Leu Phe Tyr Gly Asp Phe
                405                 410                 415

Val Gly Asp Ile Ser Glu Ala Val Ile Gln Lys Phe Leu Tyr Leu Gly
                420                 425                 430

Asp Asp Arg Asn Ile Glu Glu Val Tyr Val Gly Gly Lys Gln Val Val
            435                 440                 445

Pro Phe Ser Ser Ser Val
    450
```

<210> SEQ ID NO 8
<211> LENGTH: 3241
<212> TYPE: DNA
<213> ORGANISM: Mus musculus
<220> FEATURE:
<221> NAME/KEY: CDS
<222> LOCATION: (98)..(1462)

<400> SEQUENCE: 8

```
agagccagca gctcccgctc cgcagccgca ggaaccgctc tgcgcccgcc cggtgcgccc      60
tccttggcca gtgaactcgc gctgccctgc tgcagcc atg tgt gcg gct cgg acg     115
                                         Met Cys Ala Ala Arg Thr
                                           1               5 ccg ccg ctg gcg ctc gtc ttc cga ggg act ttc gtc cac tcc acc tgg      163
Pro Pro Leu Ala Leu Val Phe Arg Gly Thr Phe Val His Ser Thr Trp
        10                  15                  20 acc tgc ccc atg gag gtg ctt cgc gat cac ctc ctc ggc gtg agc gac      211
Thr Cys Pro Met Glu Val Leu Arg Asp His Leu Leu Gly Val Ser Asp
    25                  30                  35
```

```
agc ggc aaa ata gtg ttt cta gaa gaa tca tct cag caa gaa aaa ctg        259
Ser Gly Lys Ile Val Phe Leu Glu Glu Ser Ser Gln Gln Glu Lys Leu
     40                  45                  50 gcc aag gag tgg tgy ttc aaa cca tgt gag atc aga gaa ctg agc cac        307
Ala Lys Glu Trp Cys Phe Lys Pro Cys Glu Ile Arg Glu Leu Ser His
 55                  60                  65                  70 cat gag ttc ttc atg cca ggc ctt gtt gat acc cac atc cat gcc cct        355
His Glu Phe Phe Met Pro Gly Leu Val Asp Thr His Ile His Ala Pro
                     75                  80                  85 cag tat gcc ttt gct gga agc aac gtt gac ctg ccg ctt ttg gag tgg        403
Gln Tyr Ala Phe Ala Gly Ser Asn Val Asp Leu Pro Leu Leu Glu Trp
                 90                  95                 100 ctg aat aag tat aca ttt ccc aca gaa caa agg ttc cgg agc act gat        451
Leu Asn Lys Tyr Thr Phe Pro Thr Glu Gln Arg Phe Arg Ser Thr Asp
             105                 110                 115 gtg gct gaa gaa gtc tac act aga gtt gtt agg aga aca ctg aag aac        499
Val Ala Glu Glu Val Tyr Thr Arg Val Val Arg Arg Thr Leu Lys Asn
120                 125                 130 ggc acc acc acg gct tgc tac ttt gga aca att cac act gac tca tcc        547
Gly Thr Thr Thr Ala Cys Tyr Phe Gly Thr Ile His Thr Asp Ser Ser
135                 140                 145                 150 ctg atc ctt gcg gaa att aca gat aaa ttt ggg cag cga gca ttt gtg        595
Leu Ile Leu Ala Glu Ile Thr Asp Lys Phe Gly Gln Arg Ala Phe Val
                    155                 160                 165 ggc aaa gta tgc atg gat ttg aat gat act gtt cca gaa tac aag gag        643
Gly Lys Val Cys Met Asp Leu Asn Asp Thr Val Pro Glu Tyr Lys Glu
                170                 175                 180 acc acc gag gag tca gtc aag gag aca gag aga ttt gtg tca gaa atg        691
Thr Thr Glu Glu Ser Val Lys Glu Thr Glu Arg Phe Val Ser Glu Met
            185                 190                 195 ctg caa aag aat tat cca agg gtg aaa ccc ata gtg acc cca cgc ttt        739
Leu Gln Lys Asn Tyr Pro Arg Val Lys Pro Ile Val Thr Pro Arg Phe
        200                 205                 210 acc ctt tct tgc acg gag act ctg atg agt gaa ctt ggc aac atc gcc        787
Thr Leu Ser Cys Thr Glu Thr Leu Met Ser Glu Leu Gly Asn Ile Ala
215                 220                 225                 230 aag acc cat gat ctg tac atc cag agc cat ata agt gaa aat cgt gaa        835
Lys Thr His Asp Leu Tyr Ile Gln Ser His Ile Ser Glu Asn Arg Glu
                235                 240                 245 gaa att gaa gcc gtg aaa agc tta tac cct agt tac aaa aac tac aca        883
Glu Ile Glu Ala Val Lys Ser Leu Tyr Pro Ser Tyr Lys Asn Tyr Thr
            250                 255                 260 gat gtc tat gat aaa aac aat ctt ctg aca aac aag aca gta atg gca        931
Asp Val Tyr Asp Lys Asn Asn Leu Leu Thr Asn Lys Thr Val Met Ala
        265                 270                 275 cat ggc tgc tac ctt tct gaa gaa gaa ctt aac atc ttc agt gaa cga        979
His Gly Cys Tyr Leu Ser Glu Glu Glu Leu Asn Ile Phe Ser Glu Arg
280                 285                 290 gga gca tcc att gca cat tgt ccc aac tct aat ctg tcg ctg agc agt       1027
Gly Ala Ser Ile Ala His Cys Pro Asn Ser Asn Leu Ser Leu Ser Ser
295                 300                 305                 310 ggc tta ctg aac gtg ctt gag gtc ctg aag cat aaa gtg aag ata ggg       1075
Gly Leu Leu Asn Val Leu Glu Val Leu Lys His Lys Val Lys Ile Gly
                315                 320                 325 ctg ggg aca gat gtg gct ggt ggc tac tcc tat tcc atg ctt gat gcc       1123
Leu Gly Thr Asp Val Ala Gly Gly Tyr Ser Tyr Ser Met Leu Asp Ala
            330                 335                 340 atc aga aga gca gtc atg gtt tcc aat gtc ctc tta att aat aag gta       1171
Ile Arg Arg Ala Val Met Val Ser Asn Val Leu Leu Ile Asn Lys Val
345                 350                 355
```

```
aat gag aaa aac ctc acc ctc aaa gaa gtc ttc aga cta gcc act ctt    1219
Asn Glu Lys Asn Leu Thr Leu Lys Glu Val Phe Arg Leu Ala Thr Leu
    360                 365                 370 gga gga agc caa gcc ctg ggg ctt gat agc gag att gga aac ttt gaa    1267
Gly Gly Ser Gln Ala Leu Gly Leu Asp Ser Glu Ile Gly Asn Phe Glu
375                 380                 385                 390 gtt ggc aag gaa ttt gat gcc ctc ttg atc aac ccc aga gca tca gac    1315
Val Gly Lys Glu Phe Asp Ala Leu Leu Ile Asn Pro Arg Ala Ser Asp
                395                 400                 405 tct ccc att gat ctg ttt tat ggg gat ttt gtt ggt gat att tct gag    1363
Ser Pro Ile Asp Leu Phe Tyr Gly Asp Phe Val Gly Asp Ile Ser Glu
            410                 415                 420 gct gtt atc cag aag ttt ctt tat cta gga gac gac cga aat att gag    1411
Ala Val Ile Gln Lys Phe Leu Tyr Leu Gly Asp Asp Arg Asn Ile Glu
        425                 430                 435 gag gtt tat gtg ggt gga aag cag gtc gtt cca ttc tcc agc tca gtg    1459
Glu Val Tyr Val Gly Gly Lys Gln Val Val Pro Phe Ser Ser Ser Val
    440                 445                 450 taa ggaccttgga catctgcgac attctcctgg aagacatga ttccgccatc          1512 ttccttgtgc ccagggacca atcagaaagt atatttacaa aaaagtaccg tgttctttgg  1572
atgacttctg ttcctgtgtc tccttccagt gcccacttgg taaattgttt gaagggagtg  1632
cgctgcttct ccactccagt ctgggagcat tgtaattca tgcacagtgcc tcccattggg  1692 ctgtttagat ttgcattgtg ctcgcacaga agacattgtt aacagctggc aatgcgcttc  1752
caatagtgaa gtaaaacgtt tccatatagg gaaatacagg acgaggagat ctccctatgt  1812
ggctagacac tctgtgctaa tgactaagaa aattaggaaa ctccagtatg gaccaatgag  1872 cagatttta tgagagggca caagctagac attgaaaaga cattggaaaa gtcattggtt   1932
gtgcttggaa atttaatata gagaacagtc tcgtaaaagg agaacctact ggatttaaaa  1992
catgcttcta gatcgacatt gtctatggac atttgcactt tgtgaaattt gcatttcagg  2052
atgtgttatt gttatgcttt cccttcttgg gatgaatgtc agaacctgaa tgccacacgc  2112
ttttcaaata tagttctatg cttcaaagtg ttcggcagaa gttgagtatt aaagatttaa  2172
agtctcttag ggatagtatt cacatagccg caaggcataa atagttgtgt ttttttgtgt  2232
gtgtgtgtac ttcaaagtca tcttgattcc tggctgtgag gtgttccagt tgcttctgtt  2292
ttattagatg agaaacaagc cctgtgtgtt gctgctctgt agactggagt tttcataaat  2352
cggggaagta ctatattccc cggagttggt gacactgagg ggacagggtt ctttgcaatg  2412
ctgaatctac ccaacgcata atcattgctg tacagttcac cctcctatca atgtgctaga  2472
acttaaaagc caagtgcaag tccctaaagc attatggata aggctctgca aggccagtat  2532
actgaaagag ctctgtgtgt gtttgtttgt tgttcgtttt gttttaatttt accaaattgt  2592 cattgtaatt cttgaagatt tttctggcat taaaatctta gaatagtgaa aaggatataa  2652
aaattccatc taatgtttat atttctagga cttacctgta ctagacatca aggaatatta  2712
aacaaaagag ggcctttag cttttctaac gtatatggtg tcccttctca tattagaact   2772
aaaaccaggt cataaccacg tggcagagct ttaggaaaca gtgatgtgta ttctacttaa  2832
atactacatt tttcttaatt aattccacct cctataaaca agcaagggcc aggaacaggt  2892
tttattaaca tatatttcac tcctagggtt taggtgagtt tccattgtat cttataacag  2952
agaaacccat taggcagtag ttagttctca catctaagaa cacacagttc ttctgttctc  3012
tatgctaact cagcagtaac ttgtccagat ctatttttcct ggtagaagca cttttagatc  3072
```

```
tggtgtgtat acattatatc tcaagatggt acacatttag gtcgtactttt gttttatttt    3132 gagaaagaaa gaaagaaaga aagaaagaaa gaaagaaaga aagaaagaaa gaaagaaaga    3192
aaaagaaagg aaggaaggaa ggaaggaaga aagaaagaaa gaaagaaag                3241
```